United States Patent
Hanson

(10) Patent No.: US 6,613,880 B2
(45) Date of Patent: Sep. 2, 2003

(54) PIPECOLIC ACID DERIVATIVES OF PROLINE THREONINE AMIDES USEFUL FOR THE TREATMENT OF RHEUMATOID ARTHRITIS

(75) Inventor: Gunnar J. Hanson, Skokie, IL (US)

(73) Assignee: Pharmacia Corporation, St. Louis, MO (US)

( * ) Notice: Subject to any disclaimer, the term of this patent is extended or adjusted under 35 U.S.C. 154(b) by 0 days.

(21) Appl. No.: 09/793,676

(22) Filed: Feb. 26, 2001

(65) Prior Publication Data

US 2001/0027247 A1 Oct. 4, 2001

Related U.S. Application Data

(63) Continuation of application No. 09/277,588, filed on Mar. 26, 1999, now abandoned, which is a continuation of application No. 09/062,525, filed on Apr. 17, 1998, now abandoned, which is a continuation of application No. 08/483,237, filed on Jun. 7, 1995, now abandoned.

(51) Int. Cl.[7] .................................................. C07K 7/00
(52) U.S. Cl. .......................... 530/330; 530/329; 514/17
(58) Field of Search ................................. 530/329, 330; 514/17

(56) References Cited

PUBLICATIONS

Hammer, Proc. Natl. Acad. Sci 91, 4456–60, 1994.*

* cited by examiner

Primary Examiner—Christopher S. F. Low
Assistant Examiner—David Lukton
(74) Attorney, Agent, or Firm—J. Timothy Keane; Joseph R. Schuh

(57) ABSTRACT

Non-peptidic compounds characterized by containing a segment condensed from pipecolic acid, aspartic acid, proline and threonine, or derivatives thereof, are useful to treat autoimmune diseases and inflammatory conditions. Compounds of particular interest are those of the formula:

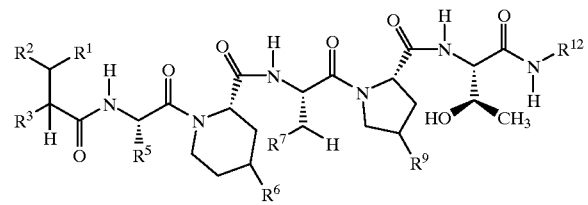

wherein $R^1$ is phenyl or cyclohexyl; wherein $R^2$ is hydrido or methyl; wherein $R^3$ is selected from hydrido, hydroxy, acetylamino, acetyl(Lys/Tyr/Thr)NH—, propionylamino and benzyloxycarbonylamino; wherein $R^5$ is selected from isopropyl, isobutyl, n-propyl, n-butyl, aminopropyl, aminobutyl, phenyl, benzyl, hydroxyphenyl, hydroxybenzyl, morpholinocarbonylethyl, morpholinocarbonylpropyl, piperazinocarbonylethyl, piperazinocarbonylpropyl, pyridinylcarbonylethyl, pyridinylcarbonylpropyl, oxazolylcarbonylethyl, oxazolylcarbonylpropyl, azepinylcarbonylethyl and azepinylcarbonylethyl; wherein $R^6$ is selected from hydrido, methyl, hydroxy, methoxy, phenyl and aminocarbonyl; wherein $R^7$ is carboxyl or methylthiomethyl; wherein $R^9$ is selected from hydrido, hydroxy, methoxy and phenyl; wherein $R^{12}$ is selected from methyl, ethyl, propyl, butyl, isobutyl, —CH(iBu)CH$_2$OH and —CH(iBu)CONH$_2$; or a pharmaceutically-acceptable amide, ester or salt thereof. A disease state of particular interest for use of the compounds would be rheumatoid arthritis.

8 Claims, No Drawings

SEQUENCE LISTING

```
<160> NUMBER OS SEQ ID NOS: 6

<210> SEQ ID NO 1
<211> LENGTH: 5
<212> TYPE: PRT
<213> ORGANISM: synthetic
<220> FEATURE:
<221> NAME/KEY: misc_feature
<222> LOCATION: (2)..(2)
<223> OTHER INFORMATION: Xaa is pipecolic acid (pec)
<220> FEATURE:
<221> NAME/KEY: mod_res
<222> LOCATION: (3)..(3)
<223> OTHER INFORMATION: modified with benzyloxy (OBn)
<220> FEATURE:
<221> NAME/KEY: mod_res
<222> LOCATION: (5)..(5)
<223> OTHER INFORMATION: modified with benzyloxy (OBn)

<400> SEQUENCE: 1

Lys Xaa Asp Pro Thr
```

<210> SEQ ID NO 2
<211> LENGTH: 6
<212> TYPE: PRT
<213> ORGANISM: synthetic
<220> FEATURE:
<221> NAME/KEY: misc_feature
<222> LOCATION: (1)..(1)
<223> OTHER INFORMATION: Xaa is 3-cyclohexylbutyric acid (CBA)
<220> FEATURE:
<221> NAME/KEY: misc_feature
<222> LOCATION: (3)..(3)
<223> OTHER INFORMATION: Xaa is pipecolic acid
<220> FEATURE:
<221> NAME/KEY: mod_feature
<222> LOCATION: (4)..(4)
<223> OTHER INFORMATION: modified with benzyloxy (OBn)
<220> FEATURE:
<221> NAME/KEY: mod_feature
<222> LOCATION: (6)..(6)
<223> OTHER INFORMATION: modified with benzyloxy (OBn)

<400> SEQUENCE: 2

Xaa Val Xaa Asp Pro Thr
1               5

<210> SEQ ID NO 3
<211> LENGTH: 6
<212> TYPE: PRT
<213> ORGANISM: synthetic
<220> FEATURE:
<221> NAME/KEY: misc_feature
<222> LOCATION: (1)..(1)
<223> OTHER INFORMATION: Xaa is 3-cyclohexylbutyric acid (CBA)
<220> FEATURE:
<221> NAME/KEY: misc_feature
<222> LOCATION: (3)..(3)
<223> OTHER INFORMATION: Xaa is pipecolic acid (pec)
<220> FEATURE:
<221> NAME/KEY: mod_res
<222> LOCATION: (4)..(4)
<223> OTHER INFORMATION: modified with benzyloxy (OBn)
<220> FEATURE:
<221> NAME/KEY: mod_res
<222> LOCATION: (6)..(6)
<223> OTHER INFORMATION: modified with benzyloxy (OBn)

<400> SEQUENCE: 3

Xaa Lys Xaa Asp Pro Thr
1               5

<210> SEQ ID NO 4
<211> LENGTH: 6
<212> TYPE: PRT
<213> ORGANISM: synthetic
<220> FEATURE:
<221> NAME/KEY: misc_feature
<222> LOCATION: (1)..(1)
<223> OTHER INFORMATION: Xaa is 3-cyclohexylbutyric acid (CBA)
<220> FEATURE:
<221> NAME/KEY: misc_feature
<222> LOCATION: (3)..(3)
<223> OTHER INFORMATION: Xaa is pipecolic acid

<400> SEQUENCE: 4

Xaa Val Xaa Asp Pro Thr
1               5

<210> SEQ ID NO 5
<211> LENGTH: 5
<212> TYPE: PRT

```
<213> ORGANISM: synthetic
<220> FEATURE:
<221> NAME/KEY: misc_feature
<222> LOCATION: (1)..(1)
<223> OTHER INFORMATION: Xaa is 3-cyclohexylbutyric acid (CBA)
<220> FEATURE:
<221> NAME/KEY: misc_feature
<222> LOCATION: (3)..(3)
<223> OTHER INFORMATION: Xaa is pipecolic acid (pec)

<400> SEQUENCE: 5

Xaa Lys Xaa Pro Thr
1               5

<210> SEQ ID NO 6
<211> LENGTH: 6
<212> TYPE: PRT
<213> ORGANISM: synthetic
<220> FEATURE:
<221> NAME/KEY: misc_feature
<222> LOCATION: (1)..(1)
<223> OTHER INFORMATION: Xaa is 3-cyclohexylpropionic acid (CPA)
<220> FEATURE:
<221> NAME/KEY: misc_feature
<222> LOCATION: (3)..(3)
<223> OTHER INFORMATION: Xaa is pipecolic acid

<400> SEQUENCE: 6

Xaa Lys Xaa Asp Pro Thr
1               5
```

PIPECOLIC ACID DERIVATIVES OF PROLINE THREONINE AMIDES USEFUL FOR THE TREATMENT OF RHEUMATOID ARTHRITIS

This application is a continuation of Ser. No. 09/277,588, filed Mar. 26, 1999, now abandoned, which is a continuation of Ser. No. 09/062,525, filed Apr. 17, 1998, now abandoned, which is a continuation of Ser. No. 08/483,237, filed Jun. 7, 1995, now abandoned.

FIELD OF THE INVENTION

Non-peptidic compounds are described for treatment of autoimmune diseases. Of particular interest are pipecolic acid derivatives compounds incorporating a characterizing segment condensed from pipecolic acid, aspartic acid, proline and threonine, or derivatives thereof, which compounds are useful to treat rheumatoid arthritis.

BACKGROUND OF THE INVENTION

Rheumatoid arthritis (RA) is an autoimmune disease characterized by chronic inflammation of the synovium. This disease is triggered by an immune response generated via the molecular recognition of the T-cell receptor on CD4-positive T cells with a complex of disease-inducing peptides bound to Human Leukocyte Antigen (HLA) class II molecules.

Rheumatoid arthritis (RA) is associated with the expression of certain HLA class II molecules, particularly the DR4-dw4, as well as DR1 and DR4-dw14. It is known that blockade of the interaction between a given class II molecule, peptide ligand, and T cell receptor inhibits specific T cell responses both in vitro and in vivo. It is further known that blockade of the above interaction in animal models of autoimmunity prevents or ameliorates autoimmune disease. Inhibitor compounds which block the binding of disease-inducing peptides to an RA-associated HLA molecule, but which will not interfere with a patient's ability to generate other class II-restricted immune responses, constitutes a selective immunosuppressive anti-RA therapy. Compounds which compete with disease-inducing endogenous peptides for binding to RA-associated HLA molecules and may thereby inhibit disease.

Other therapeutic strategies which are directed at the T cell, such as total lymphoid irradiation, thoracic duct drainage, cyclosporin A, anti-CD4 monoclonal antibody, and other monoclonal antibodies directed at T cell determinants, result in some cases in clinical improvement of rheumatoid arthritis, but these therapies are also associated with side effects. For instance, conventional general immunosuppressives increase the risk of opportunistic infections and cancer.

PCT App Pub #WO 93/05011, published Mar. 18, 1993, describes a series of oligopeptides, typically comprised of ten or more amino acids, which bind to HLA Class II molecules for indication against autoimmune diseases These larger peptides incorporating proteogenic amino acids can have poor oral bioavailability and poor plasma stability, as well as difficulty in penetrating cell membranes for proper tissue distribution.

A series of heptapeptides, such as recently reported to bind to HLA Class II molecules, similarly comprising natural, mammalian amino acids, unblocked at the C and N termini, are likely to be unstable in vivo and to possess poor bioavailability [Hammer et al, *PNAS*, 91, 4456–4460 (1994)].

DESCRIPTION OF THE INVENTION

Treatment of an autoimmune or inflammatory disease, or a hypersensitive reaction of the acute or delayed type, or an allergic reaction or asthmatic disorder, or treatment of dermatitis, arthritis, meningitis, granulomas, vasculitis or septic shock, may be accomplished by preventing or suppressing an immune response in a treatment subject by use of a pipecolic acid derivative of a proline threonine amide selected from a family of compounds of general Formula I:

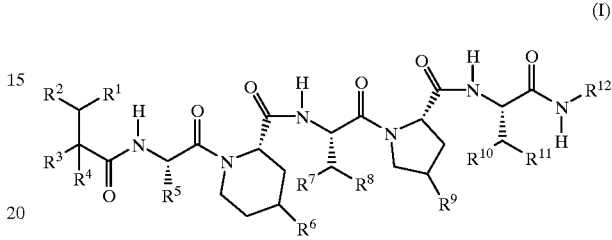

wherein $R^1$ is selected from alkyl, phenyl, cycloalkyl rings having four to ten ring-member carbon atoms, bicycloalkyl fused ring systems having seven to nine ring-member carbon atoms, heteroaryl, heteroarylalkyl, benzo-fused-heteroaryl and benzo-fused-heteroarylalkyl wherein said heteroaryl moiety or fragment is a 5- or 6-ring-member fully-unsaturated ring system having one hetero atom as a ring member, said hetero atom selected from oxygen, nitrogen and sulfur atoms, and wherein any of said heteroaryl, heteroarylalkyl, benzo-fused-heteroaryl and benzo-fused-heteroarylalkyl may be attached to the nucleus of Formula I as an $R^1$ substituent through a bond formed at any said ring-member atom or any atom of the alkyl portion of said $R^1$ substituent where said bond is capable of forming a stable compound;

wherein $R^2$ is selected from hydrido, lower alkyl, cyclohexyl and phenyl;

wherein $R^3$ is selected from hydrido, hydroxy, lower alkyl, phenyl, acetyl(Lys)NH—, acetyl(Tyr)NH—, acetyl(Thr)NH—, acetylamino, propionylamino and benzyloxycarbonylamino;

wherein $R^4$ is selected from hydrido, lower alkyl and phenyl;

wherein $R^5$ is selected from hydrido, lower alkyl, phenyl, benzyl, hydroxyphenyl, hydroxybenzyl, aminoalkyl, mono-alkyl-substituted-aminoalkyl and radicals provided by B-Het-A;

wherein Het is selected from heteroaryl moieties consisting of monocyclic and fused bicyclic ring systems having a total of five to fourteen ring members and with one to six ring members being selected from hetero atoms provided by oxygen, nitrogen and sulfur atoms, wherein said monocyclic ring system and at least one ring system of said fused bicyclic ring system is fully unsaturated, and wherein Het is further selected from heterocyclic moieties consisting of monocyclic and fused polycyclic ring systems having a total of four to twelve ring members and with one to six ring members selected from hetero atoms provided by oxygen, nitrogen and sulfur atoms, wherein said monocyclic ring-system and at least one ring system of said fused polycyclic ring system is fully saturated or partially unsaturated, wherein A is a single covalent bond or is a divalent radical selected from

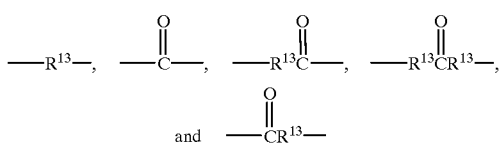

and wherein $R^{13}$ is lower alkyl;
wherein B is one or more substituents attached at a substitutable position on Het of Het-A, said substituent selected from hydrido, hydroxy, alkyl, cycloalkyl, cycloalkylalkyl, alkoxy, hydroxyalkyl, alkoxyalkyl, carboxy, alkenyl, alkynyl, halo, haloalkyl, oxo, cyano, benzyl and phenyl;
wherein $R^6$ is selected from hydrido, lower alkyl, hydroxy, alkoxy, alkoxyalkyl, carboxyalkyl, alkoxycarbonyl, alkoxycarbonyloxy, aminoalkyl, monoalkyl-substituted-aminoalkyl, amido and amidoalkyl;
wherein $R^7$ is selected from carboxyl, lower alkyl, amido and methylthiomethyl;
wherein $R^8$ is selected from hydrido, methyl and ethyl;
wherein $R^9$ is selected from hydrido, lower alkyl, alkoxy and phenyl;
wherein $R^{10}$ is hydrido or hydroxy;
wherein $R^{11}$ is hydrido or methyl;
wherein $R^{12}$ is selected from lower alkyl, phenyl, phenylalkyl, cycloalkyl, cycloalkylalkyl,

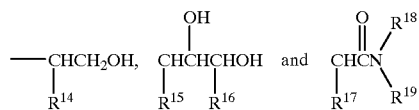

wherein each of $R^{14}$ through $R^{17}$ is independently selected from hydrido, hydroxy, alkyl, hydroxyalkyl, alkoxy, alkoxyalkyl, cycloalkyl, cycloalkylalkyl, halo, haloalkyl, cyano, benzyl and phenyl;
wherein each of $R^{18}$ and $R^{19}$ is independently selected from hydrido, alkyl, cycloalkyl, cycloalkylalkyl, benzyl and phenyl;
or a pharmaceutically-acceptable amide, ester or salt thereof.

Examples of heteroaryl 5- or 6-ring member monocyclic ring systems and benzo-fused bicyclic ring systems, having one hetero atom as a ring member selected from oxygen, nitrogen and sulfur atoms, and which ring systems are fully unsaturated, i.e. "aromatic" in character, in at least one ring, are as follow:

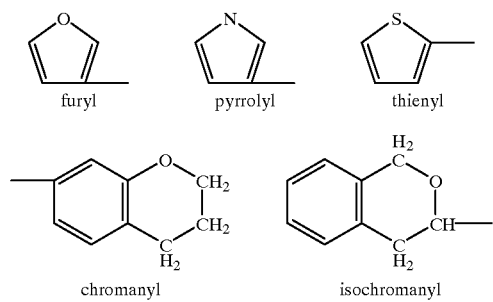

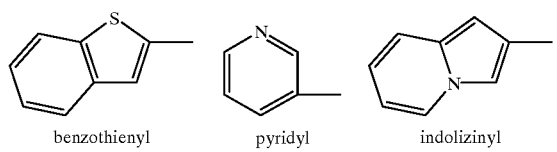

benzothienyl    pyridyl    indolizinyl

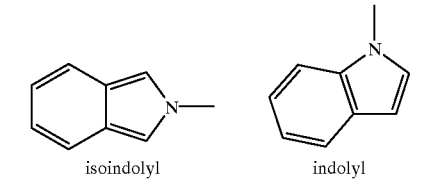

isoindolyl    indolyl

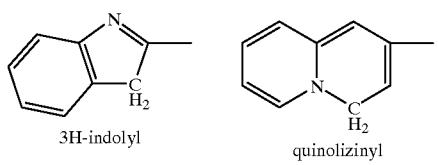

3H-indolyl    quinolizinyl

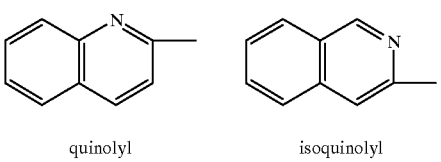

quinolyl    isoquinolyl

Examples of heterocyclic-type monocyclic or polycyclic ring systems having four to twelve ring members with one to six hetero atoms as ring members, said hetero atoms selected from oxygen, nitrogen and sulfur atoms, and wherein at least one of such ring systems is fully saturated or partially unsaturated, and wherein the polycyclic ring system may be composed of a benzo-fused ring, are as follow:

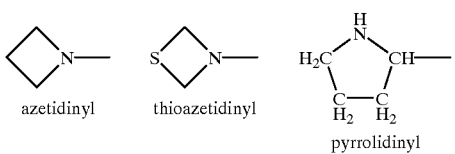

azetidinyl    thioazetidinyl    pyrrolidinyl

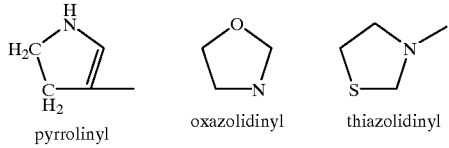

pyrrolinyl    oxazolidinyl    thiazolidinyl

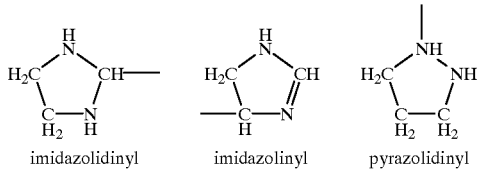

imidazolidinyl    imidazolinyl    pyrazolidinyl

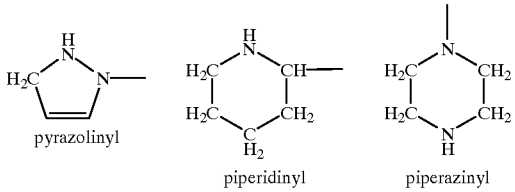

pyrazolinyl    piperidinyl    piperazinyl

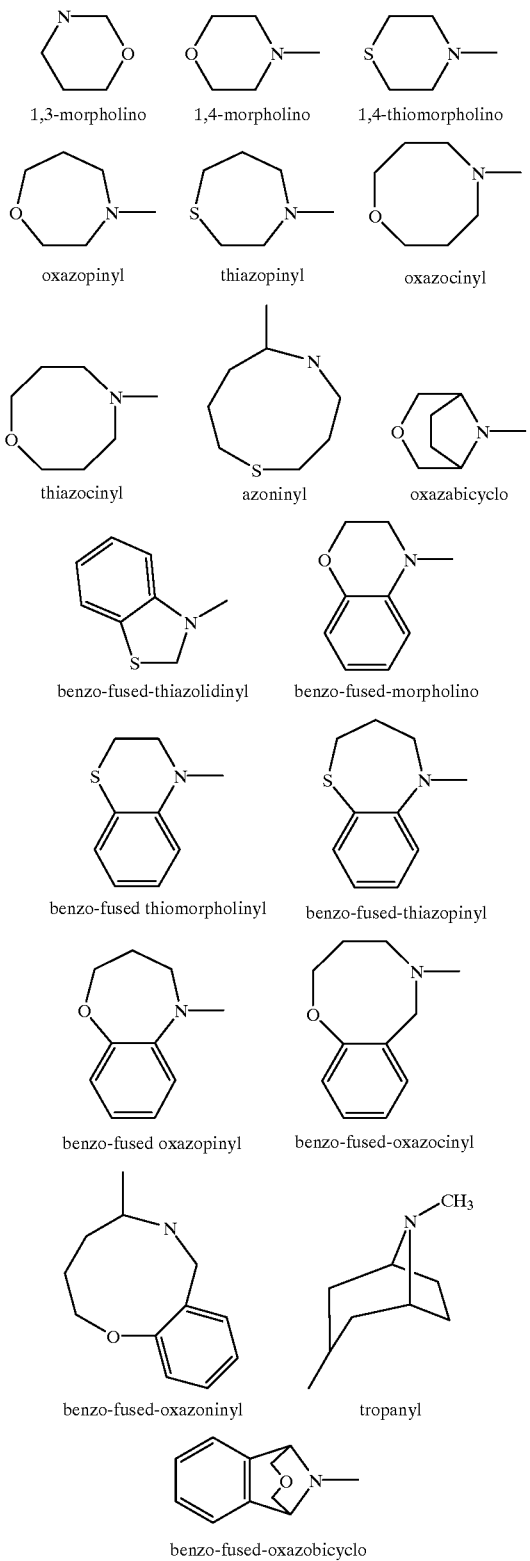
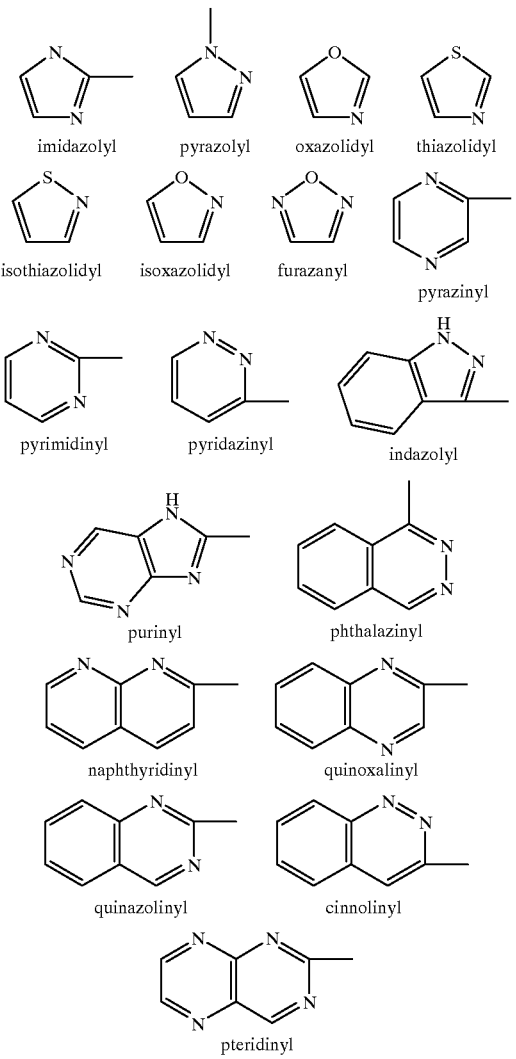

Examples of heteroaryl monocyclic and bicyclic ring systems and benzo-fused polycyclic ring systems, having one to six hetero atoms as ring members selected from oxygen, nitrogen and sulfur atoms, and which ring systems are fully unsaturated, i.e. "aromatic" in character, in at least one of the ring system, are as follow:

A preferred family of compounds consists of compounds of Formula I:

wherein $R^1$ is selected from cyclopentyl, cyclohexyl, cycloheptyl, norbornanyl, phenyl, furyl, pyrrolyl, thienyl, chromanyl, isochromanyl, benzothienyl, pyridyl, indolizinyl, isoindolyl, indolyl, 3H-indolyl, quinolizinyl, quinolyl, isoquinolyl, azetidinyl, thioazetidinyl, pyrrolidinyl, pyrrolinyl, oxazolidinyl,thiazolidinyl, imidazolidinyl, imidazolinyl, pyrazolidinyl, pyrazolinyl, piperidinyl, piperazinyl, 1,3-morpholino, 1,4-morpholino, 1,4-thiomorpholino, azepinyl, oxazopinyl, thiazopinyl, oxazocinyl, thiazocinyl, azoninyl, oxazabicyclo, benzo-fused-oxazolidinyl, benzo-fused-thiazolidinyl, benzo-fused-morpholino, benzo-fused thiomorpholinyl, benzo-fused-thiazopinyl, benzo-fused oxazopinyl, benzo-fused-oxazocinyl, benzo-fused-oxazoninyl, tropanyl and benzo-fused-oxazobicyclo;

wherein $R^2$ is selected from hydrido, methyl, ethyl, propyl, cyclohexyl and phenyl;

wherein $R^3$ is selected from hydrido, hydroxy, methyl, ethyl, phenyl, acetyl(Lys)NH—, acetyl(Tyr)NH—, acetyl(Thr)NH—, acetylamino, propionylamino and benzyloxycarbonylamino;

wherein $R^4$ is hydrido or methyl;

wherein $R^5$ is selected from hydrido, n-propyl, isopropyl, n-butyl, isobutyl, phenyl, benzyl, hydroxyphenyl, hydroxybenzyl, aminopropyl, aminobutyl and radicals provided by B-Het-R$^{13}$ and

B-Het-CR$^{13}$;

wherein Het is selected from furyl, pyrrolyl, thienyl, chromanyl, isochromanyl, benzothienyl, pyridyl, indolizinyl, isoindolyl, indolyl, 3H-indolyl, quinolizinyl, quinolyl, isoquinolyl, imidazolyl, pyrazolyl, oxazolidyl, thiazolidyl, isothiazolidyl, isoxazolidyl, furazanyl, pyrazinyl, pyrimidinyl, pyridazinyl, indazolyl, purinyl, phthalazinyl, naphthyridinyl, quinoxalinyl, quinazolinyl, cinnolinyl, pteridinyl, thieno-furanyl, furopyranyl, pyrido-oxazinyl, pyrazolo-oxazolyl, imidazo-thiazolyl, pyrazino-pyridazinyl, imidazo-thiazolyl, oxothiolo-pyrrolyl, imidazo-triazinyl, benzoxazinyl, azetidinyl, thioazetidinyl, pyrrolidinyl, pyrrolinyl, oxazolidinyl, thiazolidinyl, imidazolidinyl, imidazolinyl, pyrazolidinyl, pyrazolinyl, piperidinyl, piperazinyl, 1, 3-morpholino, 1,4-morpholino, 1,4-thiomorpholino, azepinyl, oxazopinyl, thiazopinyl, oxazocinyl, thiazocinyl, azoninyl, oxazabicyclo, benzo-fused-oxazolidinyl, benzo-fused-thiazolidinyl, benzo-fused-morpholino, benzo-fused thiomorpholinyl, benzo-fused-thiazopinyl, benzo-fused oxazopinyl, benzo-fused-oxazocinyl, benzo-fused-oxazoninyl, tropanyl and benzo-fused-oxazobicyclo;

wherein R$^{13}$ is lower alkyl;

wherein B is one or more substituents attached at a substitutable position on Het, said substituent selected from hydrido, hydroxy, alkyl, cycloalkyl, cycloalkylalkyl, alkoxy, hydroxyalkyl, alkoxyalkyl, oxo, benzyl and phenyl;

wherein R$^6$ is selected from hydrido, lower alkyl, hydroxy, methoxy carboxyalkyl, alkoxycarbonyl, alkoxycarbonyloxy, aminoalkyl, mono-alkyl-substituted-aminoalkyl, amido and amidoalkyl;

wherein R$^7$ is selected from carboxyl, lower alkyl, amido and methylthiomethyl;

wherein R$^8$ is hydrido or methyl;

wherein R$^9$ is selected from hydrido, lower alkyl, methoxy and phenyl;

wherein R$^{10}$ is hydrido or hydroxy;

wherein R$^{11}$ is hydrido or methyl;

wherein R$^{12}$ is selected from lower alkyl, phenyl, benzyl, phenylethyl, cyclohexylethyl,

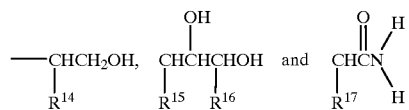

wherein each of R$^{14}$ through R$^{17}$ is independently selected from hydrido, hydroxy and alkyl;

or a pharmaceutically-acceptable amide, ester or salt thereof.

A more preferred family of compounds consists of compounds of Formula I:

wherein R$^1$ is selected from cyclopentyl, cyclohexyl, cycloheptyl, norbornanyl, phenyl, azetidinyl, thioazetidinyl, pyrrolidinyl, pyrrolinyl, oxazolidinyl, thiazolidinyl, imidazolidinyl, imidazolinyl, pyrazolidinyl, pyrazolinyl, piperidinyl, piperazinyl 1,3-morpholino, 1,4-morpholino, 1,4-thiomorpholino, azepinyl, oxazopinyl, thiazopinyl, oxazocinyl, thiazocinyl, azoninyl, oxazabicyclo and tropanyl;

wherein R$^2$ is selected from hydrido, methyl, ethyl, propyl, acetyl(Lys)NH—, acetyl(Tyr)NH—, acetyl(Thr)NH—, cyclohexyl and phenyl;

wherein R$^3$ is selected from hydrido, hydroxy, methyl, ethyl, phenyl, acetylamino, propionylamino and benzyloxycarbonylamino;

wherein R$^4$ is hydrido or methyl;

wherein R$^5$ is selected from hydrido, n-propyl, isopropyl, n-butyl, isobutyl, aminopropyl, aminobutyl, phenyl, hydroxyphenyl, benzyl, hydroxybenzyl and radicals provided by

B-Het-CR$^{13}$;

wherein Het is selected from azetidinyl, pyridinyl, isoindolyl, oxazolyl, isoxazolyl, indolyl, quinolyl, isoquinolyl, azetidinyl, thioazetidinyl, pyrrolidinyl, pyrrolinyl, oxazolidinyl, thiazolidinyl, imidazolyl, imidazolidinyl, imidazolinyl, pyrazolidinyl, pyrazolinyl, piperidinyl, piperazinyl, 1,3-morpholino, 1,4-morpholino, 1,4-thiomorpholino, azepinyl, oxazopinyl, thiazopinyl, oxazocinyl, thiazocinyl, azoninyl, oxazabicyclo and tropanyl;

wherein R$^{13}$ is selected from methyl, ethyl and propyl;

wherein B is one or more substituents attached at a substitutable position on Het, said substituent selected from hydrido, hydroxy, methyl, ethyl, propyl, oxo, benzyl and phenyl;

wherein R$^6$ is selected from hydrido, methyl, hydroxy, methoxy, phenyl, alkoxycarbonyl, alkoxycarbonyloxy, aminoalkyl, mono-amido and amidoalkyl;

wherein R$^7$ is selected from carboxyl, n-propyl, n-butyl, amido and methylthiomethyl;

wherein R$^8$ is hydrido or methyl;

wherein R$^9$ is selected from hydrido, lower alkyl, methoxy and phenyl;

wherein R$^{10}$ is hydroxy;

wherein R$^{11}$ is hydrido or methyl;

wherein R$^{12}$ is selected from lower alkyl, phenyl, phenylethyl, cyclohexylethyl,

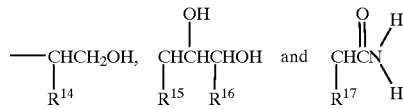

wherein each of R$^{14}$ through R$^{17}$ is independently selected from hydrido, hydroxy, methyl, ethyl, n-propyl, isopropyl, n-butyl, isobutyl, benzyl and phenyl;

or a pharmaceutically-acceptable amide, ester or salt thereof.

A highly preferred family of compounds consists of compounds of Formula I:

wherein R$^1$ is phenyl or cyclohexyl; wherein R$^2$ is hydrido or methyl; wherein R$^3$ is selected from hydrido, hydroxy, acetyl (Lys)NH—, acetyl(Tyr)NH—, acetyl(Thr)NH—, acetylamino, propionylamino and benzyloxycarbonylamino; wherein R$^4$ is hydrido; wherein R$^5$ is selected from isopropyl, isobutyl, n-propyl, n-butyl, aminopropyl, aminobutyl, phenyl, benzyl, para-hydroxyphenyl, para-hydroxybenzyl, imidazolcarbonylethyl, imidazolcarbonylpropyl, pyrrolidinylcarbonylethyl, pyrrolidinylcarbonylpropyl, azetidinylcarbonylethyl, azetidinylcarbonylpropyl, morpholinocarbonylethyl, morpholinocarbonylpropyl, piperazinocarbonylethyl, piperazinocarbonylpropyl, pyridinylcarbonylethyl, pyridinylcarbonylpropyl, oxazolylcarbonylethyl, oxazolylcarbonylpropyl, isoxazolylcarbonylethyl, isoxazolylcarbonylpropyl, azepinylcarbonylethyl and azepinylcarbonylethyl; wherein $R^6$ is selected from hydrido, methyl, hydroxy, methoxy, phenyl and aminocarbonyl; wherein $R^7$ is carboxyl or methylthiomethyl; wherein $R^8$ is hydrido; wherein $R^9$ is selected from hydrido, hydroxy, methyl, methoxy and phenyl; wherein $R^{10}$ is hydroxy; wherein $R^{11}$ is methyl; wherein $R^{12}$ is selected from methyl, ethyl, propyl, butyl, isobutyl, —CH(iBu)CH$_2$OH and —CH(iBu)CONH$_2$; or a pharmaceutically-acceptable amide, ester or salt thereof.

The term "hydrido" denotes a single hydrogen atom (H). This hydrido group may be attached, for example, to an oxygen atom to form a hydroxyl group; or, as another example, one hydrido group may be attached to a carbon atom to form a

group; or, as another example, two hydrido atoms may be attached to a carbon atom to form a —CH$_2$— group. Where the term "alkyl" is used, either alone or within other terms such as "haloalkyl" and "hydroxyalkyl", the term "alkyl" embraces linear or branched radicals having one to about twenty carbon atoms or, preferably, one to about twelve carbon atoms. More preferred alkyl radicals are "lower alkyl", radicals having one to about ten carbon atoms. Most preferred are lower alkyl radicals having one to about five carbon atoms. The term "cycloalkyl" embraces cyclic radicals having three to about ten ring carbon atoms, preferably three to about six carbon atoms, such as cyclopropyl, cyclobutyl, cyclopentyl and cyclohexyl. The term "haloalkyl" embraces radicals wherein any one or more of the alkyl carbon atoms is substituted with one or more halo groups, preferably selected from bromo, chloro and fluoro. Specifically embraced by the term "haloalkyl" are monohaloalkyl, dihaloalkyl and polyhaloalkyl groups. A monohaloalkyl group, for example, may have either a bromo, a chloro, or a fluoro atom within the group. Dihaloalkyl and polyhaloalkyl groups may be substituted with two or more of the same halo groups, or may have a combination of different halo groups. A dihaloalkyl group, for example, may have two fluoro atoms, such as difluoromethyl and difluorobutyl groups, or two chloro atoms, such as a dichloromethyl group, or one fluoro atom and one chloro atom, such as a fluoro-chloromethyl group. Examples of a polyhaloalkyl are trifluoromethyl, 1,1-difluoroethyl, 2,2,2-trifluoroethyl, perfluoroethyl and 2,2,3,3-tetrafluoropropyl groups. The term "difluoroalkyl" embraces alkyl groups having two fluoro atoms substituted on any one or two of the alkyl group carbon atoms. The terms "alkylol" and "hydroxyalkyl" embrace linear or branched alkyl groups having one to about ten carbon atoms any one of which may be substituted with one or more hydroxyl groups. The term "alkenyl" embraces linear or branched radicals having two to about twenty carbon atoms, preferably three to about ten carbon atoms, and containing at least one carbon-carbon double bond, which carbon-carbon double bond may have either cis or trans geometry within the alkenyl moiety. The term "alkynyl" embraces linear or branched radicals having two to about twenty carbon atoms, preferably two to about ten carbon atoms, and containing at least one carbon-carbon triple bond. The term "cycloalkenyl" embraces cyclic radicals having three to about ten ring carbon atoms including one or more double bonds involving adjacent ring carbons. The terms "alkoxy" and "alkoxyalkyl" embrace linear or branched oxy-containing radicals each having alkyl portions of one to about ten carbon atoms, such as methoxy group. The term "alkoxyalkyl" also embraces alkyl radicals having two or more alkoxy groups attached to the alkyl radical, that is, to form monoalkoxyalkyl and dialkoxyalkyl groups. The "alkoxy" or "alkoxyalkyl" radicals may be further substituted with one or more halo atoms, such as fluoro, chloro or bromo, to provide haloalkoxy or haloalkoxyalkyl groups. The term "alkylthio" embraces radicals containing a linear or branched alkyl group, of one to about ten carbon atoms attached to a divalent sulfur atom, such as a methythio group. Preferred aryl groups are those consisting of one, two, or three benzene rings. The term "aryl" embraces aromatic radicals such as phenyl, naphthyl and biphenyl. The term "aralkyl embraces aryl-substituted alkyl radicals such as benzyl, diphenylmethyl, triphenylmethyl, phenylethyl, phenylbutyl and diphenylethyl. The terms "benzyl" and "phenylmethyl" are interchangeable. The terms "phenalkyl" and "phenylalkyl" are interchangeable. An example of "phenalkyl" is "phenethyl" which is interchangeable with "phenylethyl". The terms "alkylaryl", "alkoxyaryl" and "haloaryl" denote, respectively, the substitution of one or more "alkyl", "alkoxy" and "halo" groups, respectively, substituted on an "aryl" nucleus, such as a phenyl moiety, which is then attached to the structure of Formula I or Formula II. The terms "aryloxy" and "arylthio" denote radicals respectively, provided by aryl groups having an oxygen or sulfur atom through which the radical is attached to a nucleus, examples of which are phenoxy and phenylthio. The terms "sulfinyl" and "sulfonyl", whether used alone or linked to other terms, denotes, respectively, divalent radicals SO and SO$_2$. The term "aralkoxy", alone or within another term, embraces an aryl group attached to an alkoxy group to form, for example, benzyloxy. The term "acyl" whether used alone, or within a term such as acyloxy, denotes a radical provided by the residue after removal of hydroxyl from an organic acid, examples of such radical being acetyl and benzoyl. "Lower alkanoyl" is an example of a more prefered sub-class of acyl. The term "amido" denotes a radical consisting of nitrogen atom attached to a carbonyl group, which radical may be further substituted in the manner described herein. The amido radical can be attached to the nucleus of a compound of Formula I or Formula II through the carbonyl moiety or through the nitrogen atom of the amido radical. The term monoalkylaminocarbonyl" is interchangeable with "N-alkylamido". The term "dialkylaminocarbonyl" is interchangeable with "N,N-dialkylamido". The term "alkenylalkyl" denotes a radical having a double-bond unsaturation site between two carbons, and which radical may consist of only two carbons or may be further substituted with alkyl groups which may optionally contain additional double-bond unsaturation. The term "heteroaryl", where not otherwised defined before, embraces aromatic ring systems containing one or two hetero atoms selected from oxygen, nitrogen and sulfur in a ring system having five or six ring members, examples of which are thienyl, furanyl, pyridinyl, thiazolyl, pyrimidyl and isoxazolyl. Such heteroaryl may be attached as a substituent through a carbon atom of the heteroaryl ring system, or may be attached through a carbon atom of a moiety substituted on a heteroaryl ring-member carbon atom, for example, through the methylene substituent of imidazolemethyl moiety. Also, such heteroaryl may be attached through a ring nitrogen atom as long as aromaticity of the heteroaryl moiety is preserved after attachment. For any of the foregoing defined radicals, preferred radicals are those containing from one to about ten carbon atoms.

Specific examples of alkyl groups are methyl, ethyl, n-propyl, isopropyl, n-butyl, sec-butyl, isobutyl, tert-butyl, n-pentyl, isopentyl, methylbutyl, dimethylbutyl and neopentyl. Typical alkenyl and alkynyl groups may have one unsaturated bond, such as an allyl group, or may have a plurality of unsaturated bonds, with such plurality of bonds either adjacent, such as allene-type structures, or in conjugation, or separated by several saturated carbons.

Also included in the combination of the invention are the isomeric forms of the above-described compounds of Formula I, including diastereoisomers, regioisomers and the pharmaceutically-acceptable salts thereof. The term "pharmaceutically-acceptable salts" embraces salts commonly used to form alkali metal salts and to form addition salts of free acids or free bases. The nature of the salt is not critical, provided that it is pharmaceutically-acceptable. Suitable pharmaceutically-acceptable acid addition salts may be prepared from an inorganic acid or from an organic acid. Examples of such inorganic acids are hydrochloric, hydrobromic, hydroiodic, nitric, carbonic, sulfuric and phosphoric acid. Appropriate organic acids may be selected from aliphatic, cycloaliphatic, aromatic, araliphatic, heterocyclic, carboxylic and sulfonic classes of organic acids, example of which are formic, acetic, propionic, succinic, glycolic, gluconic, lactic, malic, tartaric, citric, ascorbic, glucuronic, maleic, fumaric, pyruvic, aspartic, glutamic, benzoic, anthranilic, p-hydroxybenzoic, salicyclic, phenylacetic, mandelic, embonic (pamoic), methansulfonic, ethanesulfonic, 2-hydroxyethanesulfonic, pantothenic, benzenesulfonic, toluenesulfonic, sulfanilic, mesylic, cyclohexylaminosulfonic, stearic, algenic, β-hydroxybutyric, malonic, galactaric and galacturonic acid. Suitable pharmaceutically-acceptable base addition salts include metallic salts made from aluminium, calcium, lithium, magnesium, potassium, sodium and zinc or organic salts made from N,N'-dibenzylethylenediamine, chloroprocaine, choline, diethanolamine, ethylenediamine, meglumine (N-methylgluca-mine) and procaine All of these salts may be prepared by conventional means from the corresponding compound by reacting, for example, the appropriate acid or base with such compound.

Nomenclature used to define the amino acids used to make compounds of Formula I is that specified by the IUPAC [published in *European Journal of Biochemistry*, 138, 9–37 (1984)], wherein conventional representation of the peptides stipulates that in a peptide sequence the amino group appears to the left and the carboxyl group to the right. When the amino acid has enantiomeric forms, it is the L form of the amino acid which is represented unless otherwise stated. In the amino acid structural formulas, each residue is generally represented by a single or 3-letter designation, corresponding to the trivial name of the amino acid in accordance with the following list:

| TRIVIAL NAME | SYMBOL | ONE-LETTER SYMBOL |
|---|---|---|
| Alanine | Ala | A |
| Arginine | Arg | R |
| Asparagine | Asn | N |
| Aspartic Acid | Asp | D |

-continued

| TRIVIAL NAME | SYMBOL | ONE-LETTER SYMBOL |
|---|---|---|
| Cysteine | Cys | C |
| Glutamine | Gln | Q |
| Glutamic Acid | Glu | E |
| Glycine | Gly | G |
| Histidine | His | H |
| Homocysteine | Hcy | — |
| Isoleucine | Ile | I |
| Leucine | Leu | L |
| Lysine | Lys | K |
| Methionine | Met | M |
| Norvaline | Nva | — |
| Penicillamine | Pen | — |
| Phenylalanine | Phe | F |
| Praline | Pro | P |
| Serine | Ser | S |
| Threonine | Thr | T |
| Tryptophan | Trp | W |
| Tyrosine | Tyr | Y |
| Valine | Val | V |
| Unspecified Amino Acid | Xaa | X |

Another name for norvaline in n-propylglycine. The group $^{125}$I-Tyr indicates a radioactive mono-iodinated tyrosine residue.

CBA=3-cyclohexylbutyric acid
CPA=3-cyclohexylpropionic acid
Ac=acetyl
OBn=benzyloxy
Pec=pipecolic acid
Z=benzyloxycarbonyl Compounds of the present invention function as HLA "groove blockers", referring to the peptide binding pocket or "groove" present in the HLA, particularly the PR4-dw4, as well as DR1 and DR4-dw14. Because the compounds of the present invention are targeted to specific subsets of Class II molecules, greater specificity and better side-effect profiles are gained. Compounds of the present invention find utility in the treatment of other autoimmune diseases, including rheumatoid arthritis.

Thus, compounds of Formula I would be useful in suppressing immune response in a human or animal subject susceptible to or afflicted with an autoimmune disease or inflammatory disease. Examples of such treatable disease are systemic lupus erythematosis, multiple sclerosis, myesthenia gravis, thyroiditis, Grave's disease, autoimmune hemolytic anemia, autoimmune hemolytic anemia, autoimmune thrombocytopenia purpura, mixed connective tissue disease, idiopathic Addison's disease, Sjogren's syndrome, insulin dependent diabetes mellitus, rheumatoid arthritis, psoriasis, glomerulonephritis, inflammatory bowel disease and Crohn's Disease.

Compounds of Formula I would also be useful in suppressing immune response in a human or animal subject susceptible to or afflicted with an allergy, such as an asthmatic condition or reaction, urticaria or with airway hypersensitivity.

Compounds of Formula I would also be useful in suppressing immune response in a human or animal subject afflicted with or susceptible to septic shock.

Compounds of Formula I would also be useful in preventing or suppressing acute or delayed-type hypersensitivity responses or conditions resulting from or associated with hypersensitivity responses such as contact dermatitis, hemolytic anemias, antibody-induced thrombocytopenia, Goodpasture's syndrome, hypersensitivity, pneumonitis, glomerulonephritis, granulomas, thyroiditis, encephelomyelitis and meningitis.

Of particular interest is use of a compound of Formula I to treat rheumatoid arthritis.

Compounds of Formula I would also be useful in adjunct therapy involving, typically, coadministration of a second immunosuppressive compound of Formula I or coadministration of an immunosuppressive agent of a different class of compounds. Such coadministration may provide a synergistic result between a compound of Formula I and an agent selected from one or more other classes of immunosuppressants. Such synergistic result allows for a lower dosage of another immunosuppressant agent having a toxic effect, such as a cyclosporin agent or steroid agent, such as cortisone and cortisol. Thus, use of a compound of Formula I in such synergistic combination allows utilization of the immunosuppressant benefits of a cyclosporin agent or steroid agent without, or with less of, the deleterious side effects of such agent. Examples of other immunosuppressant agents include a cyclosporin compound, Fujisawa FK-506 (macrolide lactone) compound, rapamycin, a glucocorticoid, an antiproliferative agent, a monoclonal antibody such as an anti-CD3 (anti-T cell receptor antibody), anti-CD5/CD7, anti-CD4 agent, an anti-IL-2 receptor (anti-cytokine receptor antibody) agent, an anti-IL-2 (anti-cytokine antibody), Nippon NKT-01 (15-deoxyspergualin) and Syntex RS-61443.

DESCRIPTION OF SYNTHETIC METHODS FOR PREPARATION OF COMPOUNDS OF THE INVENTION

Synthesis

The compounds of Formula I can be prepared by coupling individual protected amino acid building blocks by standard solution or solid phase methods. The coupling reagents may be selected from those amide-forming reagents known in the art, such as carbodiimides, mixed carbonic anhydrides and active esters, but are not limited to these methods. The following Steps and Examples constitute specific exemplification of methods to prepare starting materials, intermediates and final compounds of Formula I. Those skilled in the art will readily understand that known variations of the conditions and processes of the following preparative procedures can be used to prepare the compounds of the Steps and Examples. All temperatures expressed are in degrees Centigrade.

Step 1

Pro-Thr(OBn)-n-propylamide Hydrochloride

Commercially available Boc-L-Thr(OBn)-OH (5 g) was mixed with 1-hydroxybenzotriazole (2.62 g), diisopropylethylamine (2.08 g) in methylene chloride (14 mL) and cooled to 0° C. To this was added 1-(3-dimethylaminopropyl)-3-ethylcarbodiimide hydrochloride, followed by n-propylamine (1.14 g) 2 minutes later. After allowing the reaction mixture to stir at 0 for 5 hours, the organic solution was washed sequentially with water, 1N hydrochloric acid, 5% sodium bicarbonate, then dried (magnesium sulfate), filtered and evaporated to obtain an oily residue. This residue was taken up in 4M hydrogen

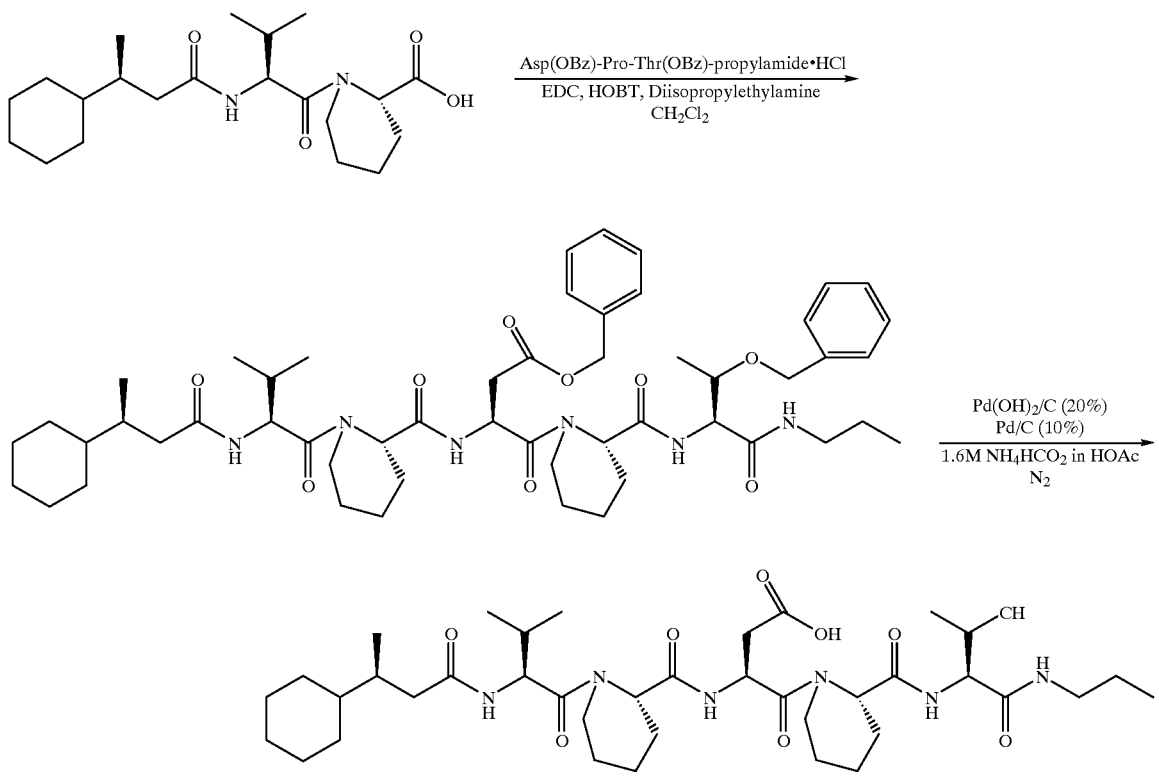

chloride in dioxane solution (50 mL) and allowed to stand at room temperature for 30 minutes. The solvent was then evaporated and the product triturated with ether. The resulting solid was collected a filter plate. A portion of this material (1.5 g) was then mixed with Boc-L-Pro-OSu (1.5 g) in methylene chloride (20 mL), cooled to 0° C., and diisopropylethylamine (675 mg) was added. After allowing the reaction mixture to stir at 0° C. for 5 hours, the organic solution was washed sequentially with water, 1N hydrochloric acid, 5% sodium bicarbonate, then dried (magnesium sulfate), filtered and evaporated to obtain an oily residue. This residue was taken up in 4 M hydrogen chloride in dioxane solution (50 mL) and allowed to stand at room temperature for 30 minutes. The solvent was then evaporated and the product triturated with ether. The resulting solid was collected a filter plate to yield the title compound (1.45 g). $^1$H NMR (400 MHz): consistent with proposed structure.

Step 2

Asp(OBn)-Pro-Thr(OBn)-n-propylamide Hydrochloride

Commercially available Boc-L-Asp(OBn)-OH (1 g) was mixed with 1-hydroxybenzotriazole (500 mg), the title compound from Step 1 (1 g) and diisopropylethylamine (736 mg) in methylene chloride (20 mL), and the solution was cooled to 0° C. To this was added 1-(3-dimethylaminopropyl)-3-ethylcarbodiimide hydrochloride (710 mg) in one portion. After allowing the reaction mixture to stir at 0° C. for 5 hours, the organic solution was washed sequentially with water, 1 N hydrochloric acid, 5% sodium bicarbonate, then dried (magnesium sulfate), filtered and evaporated to obtain an oily residue. This residue was taken up in 4 M hydrogen chloride in dioxane solution (50 mL) and allowed to stand at room temperature for 30 minutes. The solvent was then evaporated and the product triturated with ether. The resulting white solid was collected a filter plate to yield the title compound. $^1$H NMR (400 MHz): consistent with proposed structure.

Step 3

Pec-Asp(OBn)-Pro-Thr(OBn)-n-propylamide Hydrochloride

Commercially available Boc-L-pipecolic acid (Boc-Pec, 100 mg) was mixed with 1-hydroxybenzotriazole (71 mg), the title compound from Step 2 (259 mg) and diisopropylethylamine (113 mg) in methylene chloride (2 mL), and the solution was cooled to 0° C. To this was added 1-(3-dimethylaminopropyl)-3-ethylcarbodiimide hydrochloride (100 mg) in one portion. After allowing the reaction mixture to stir at 0° C. for 5 hours, the organic solution was washed sequentially with water, 1N hydrochloric acid, 5% sodium bicarbonate, then dried (magnesium sulfate), filtered and evaporated. The residue was taken up in 4M hydrogen chloride in dioxane solution (50 mL) and allowed to stand at room temperature for 30 minutes. The solvent was then evaporated and the product triturated with ether. The resulting white solid was collected a filter plate to yield the title compound (223 mg). $^1$H NMR (400 MHz): consistent with proposed structure.

Step 4

Lys(Z)-Pec-Asp(OBn)-Pro-Thr(OBn)-n-propylamide Hydrochloride

The same procedure as described in Step 3 was used to couple Boc-L-Lys(Z)-OH to the title compound of Step 3, yielding the title compound as a white solid (1.12 g)

Step 5

Val-Pec-OMe Hydrochloride

Boc-Val-OH was dissolved in $CH_2Cl_2$, and cooled to 0° C. via ice water bath. The reaction solution was treated with 1.2 eq of 1-hydroxybenzotriazole, 2 eq of diisopropylethylamine, and 1.5 eq of Pec-OMe.HCl. After all solids were dissolved, the reaction was treated with 1.2 eq of 1-(3-dimethyl-aminopropyl)-3-ethylcarbodiimide.HCl. The reaction flask was stoppered, sealed with parafilm, and placed in the refrigerator overnight. The $CH_2Cl_2$ was evaporated and replaced with EA. The organic solution was washed with water, 1.5 M HCl, and 5% $NaHCO_3$, dried over $Na_2SO_4$, and thoroughly evaporated to a clear, colorless oil. The entire sample was then dissolved in 4.0M HCl in dioxane, stirred for one hour at rt, and thoroughly evaporated to yield Val-Pec-OMe.HCl as a white foam.

Step 6

(S)-3-cyclohexylbutyryl-Val-Pec-OH ((S)-CBA-Val-Pec-OH)

Commercially available (S)-3-phenylbutyric acid treated with rhodium-on-carbon in methanol at 60 psi and 60° C. for 3.2 hours to yield (S)-3-cyclohexylbutyric acid. This acid was then converted to the acid chloride by treatment with 1 equivalent of oxalyl chloride and a catalytic amount of DMF, in toluene for 90 minutes. 250 mg of resulting (S)-3-cyclohexylbutyroyl chloride was dissolved in 10 mL ethyl acetate, and treated with 1.5 equivalents of the dipeptide, Val-Pec-OMe hydrochloride, followed by 3 equivalents of sodium bicarbonate dissolved in 2 mL of water. The reaction mixture stirred vigorously for 2 hours. The organic solution was then washed with 1.5 M HCl, dried over sodium sulfate, and evaporated to obtain a clear, colorless oil. This product was then treated with 3 equivalents of KOH dissolved in water and tetrahydrofuran and the reaction stirred vigorously for 12 hours. The tetrahydrofuran was evaporated, and the acid product was precipitated by acidifying the aqueous solution with conc. HCl. The mixture was extracted with ethyl acetate, the organic layer dried over $Na_2SO_4$, and evaporated to yield the title compound as a white foam.

Step 7 s-CBA-Val-Pec-Asp(OBn)-Pro-Thr(OBn)-propylamide 100 mg of the title compound from Step 6 ((S)-CBA-Val-Pec-OH) was dissolved in 3 mL of dichloromethane, and cooled to 0° C. via ice water bath. The clear, colorless reaction solution was then treated with 36 mg of 1-hydroxybenzotriazole, 94 mL of diisopropylethylamine, and 170 mg of Asp(OBn)-Pro-Thr(OBn)-propylamide hydrochloride, while stirring. After all solids had dissolved, the reaction solution was treated with 51 mg of 1-(3-dimethylaminopropyl)-3-ethylcarbo-dimide hydrochloride. The solution stirred at 0° C. for 1 hour. The reaction flask was then stoppered, sealed with parafilm, and placed in the refrigerator overnight. The dichloromethane solvent was then evaporated and replaced with Ethyl Acetate. The organic solution was washed with water, 1.5M HCl, and 5%$Na_2CO_3$, dried over $Na_2SO_4$, filtered, and evaporated thoroughly. The entire sample was flash chromatographed eluting with 5% MeOH/$CHCl_3$. The title compound (s-CBA-Val-Pec-Asp(OBz)-Pro-Thr(OBz)-propylamide) was successfully isolated (62 mg) as a white crystalline solid.

Step 8

(S)-3-Cyclohexylbutyroyl Chloride (S)-3-phenylbutyric acid was hydrogenated using Rh/C in MeOH at 60 psi and 60° C. for 3.2 hours. The reduced product was then converted to the title acid chloride by treating with 1 eq of oxalyl chloride, and a catalytic amount of DMF, in toluene for 90 minutes, followed by evaporation of the volatile materials.

Step 9

Thr(O-benzyl)-allyl ester Hydrochloride

To a room temperature solution of commercially available Boc-Threonine(O-benzyl)-OH (8.00 g, 25.0 mmol) and cesium carbonate (11.32 g, 34.7 mmol) in dry DMF (15.5 mL) under a $N_2$ atmosphere, was added by syringe allyl bromide (3.01 mL, 34.7 mmol). After stirring overnight the mixture was concentrated, diluted with $H_2O$ (75 mL) and extracted with ethyl acetate (3×25 mL). The combined organic layers were washed with saturated $NaHCO_3$ solution (2×25 mL), $H_2O$ (2×25 mL), and brine (25 mL), then dried with $MgSO_4$. The filtrate was concentrated to a clear, colorless oil (8.76 g). $^1$H NMR (400 MHz) data was consistent for the Boc compound. The oil was dissolved into 4 M HCl in 1,4-dioxane (100 mL) and stirred at room temperature for 30 minutes. The reaction was concentrated to a clear, yellow oil, triturated several times with $Et_2O$, and concentrated to a oil (7.40 g, 109% crude yield). $^1$H NMR (400 MHz): consistent with proposed structure.

Step 10

Pro-Thr(O-benzyl)-allyl Ester Hydrochloride

To a 0° C. solution of the title compound from Step 9 (6.80 g, 23.8 mmol) and commercially available Boc-proline-OSu (6.81 g, 21.8 mmol) in $CH_2Cl_2$ (70 mL) under a $N_2$ atmosphere, was added diisopropylethylamine (4.32 mL, 24.8 mmol). After 2h at 0° C. the solution was washed with water (20 mL), 1.0 $\underline{N}$ $KHSO_4$ solution (20 mL), saturated $NaHCO_3$ (2×20 mL), $H_2O$ (2×20 mL) and brine (20 mL). Dried over $MgSO_4$. The filtrate was concentrated and purified by medium pressure chromatography (silica gel, 30% ethyl acetate in hexane) to give a white solid (5.66 g). The solid was dissolved into 4 $\underline{N}$ HCl in 1,4-dioxane (100 mL) at room temperature. After 1 hour the solution was concentrated, triturated with $Et_2O$ several times, and concentrated to give the title compound as a sticky, white solid (4.61 g, 55% yield). $^1$H NMR (400 MHz): consistent with proposed structure.

Step 11

Asp(O-benzyl)-Pro-Thr(O-benzyl)-allyl Ester Hydrochloride

To a 0° C. solution of the tile compound from Step 10 (4.61 g, 12.0 mmol), Boc-Asp(O-benzyl)-OH (3.89 g, 12.0 mmol), 1-hydroxybenzotriazole (4.41 g, 32.6 mmol) and 4-methyl morpholine (1.39 g, 13.8 mmol) in $CH_2Cl_2$ (65 mL) under a $N_2$ atmosphere, was added 1-(3-dimethylaminopropyl)-3-ethyl-carbodiimide hydrochloride (3.28 g, 17.1 mmol). The solution was stirred at 0° C. for 1 hour and then room temperature overnight. It was then concentrated and redissolved into $CH_2Cl_2$ (100 mL), and washed with 1.0 $\underline{N}$ $KHSO_4$ solv (2×25 mL), saturated $NaHCO_3$ solv (2×25 mL), $H_2O$ (2×25 mL), and brine (25 mL). Dried over $MgSO_4$. The filtrate was concentrated and purified by medium pressure chromatography (silica gel, 30% ethyl acetate in hexane) to give a clear, colorless oil (6.88 g). The oil was dissolved into 4N HCl in dioxane at rt. After 30 minutes the solution was concentrated to a white solid, triturated with $Et_2O$ several times, and dried in a 50° C. vacuum oven to give the title compound as a white solid (4.65 g, 66% yield). $^1$H NMR (400 MHz): consistent with proposed structure. Anal. Calcd for $C_{30}H_{38}N_3O_7Cl_1$: C, 61.27; H, 6.51; N, 7.15. Found: C, 61.05; H, 6.71; N, 7.14.

Step 12

Lys(Z)-Pec-OMe hydrochloride

Commercially available Boc-Lys(Z)-OH was dissolved in dimethylformamide (DMF), and cooled to 0° C. via ice water bath. The solution was treated with 1.2 equivalents of 1-hydroxybenzotriazole, 2 equivalents of diisopropylethylamine, and 1.5 equivalents of commercially available pipecolic methyl ester hydrochloride (Pec-OMe.HCl). After all solids were dissolved, the reaction was treated with 1.2 equivalents of 1-(3-dimethyl-aminopropyl)-3-ethylcarbodiimide hydrochloride. Reaction progress was monitored by TLC. After 5 hours, the DMF was thoroughly evaporated. The oily residue was dissolved in water/ethyl acetate. The organic portion was washed with 1.5 M HCl and 5% $NaHCO_3$, dried over $MgSO_4$, and filtered. The solution was evaporated to a clear, colorless oil. The entire sample was then dissolved in 4.0 M HCl in dioxane, stirred for one hour at rt, and thoroughly evaporated to yield the title compound, Lys(Z)-Pec-OMe.HCl, as a white foam.

Step 13

(S)-CBA-Lys(Z)-Pec-OH 1.0 g of the title compound from Step 8 (S)-3-cyclohexylbutyroyl chloride was dissolved in 15 mL ethyl acetate, and treated with 1.5 equivalents (eq) of the title compound from Step 12, Lys(Z)-Pec-OMe.HCl, followed by 3 eq of $NaHCO_3$ dissolved in 5 mL of water. After 30 minutes, the organic portion was washed with water, 1.5 M HCl and 5% NaHCO$_3$. The solution was dried over Na$_2$SO$_4$ and evaporated to a clear, colorless oil (89.4%). The entire sample was chromatographed by flash column eluting with 5% MeOH/CHCl$_3$ to remove a baseline impurity. The entire sample was then hydrolyzed using 3 eq of KOH dissolved in water and tetrahydrofuran (THF) as a cosolvent. The reaction stirred vigorously for 5 hours. The THF was evaporated and the aqueous portion was acidified with concentrated HCl. The mixture was extracted with ethyl acetate, dried over Na$_2$SO$_4$, and the solution evaporated to a clear, colorless oil (72%), which was lyophilized from water to give the title compound as a white solid.

Step 14

(S)-CBA-Lys(Z)-Pec-Asp(OBn)-Pro-Thr(OBn)-allyl Ester

The title compound from Step 13 (300 mg), (S)-CBA-Lys(Z)-Pec-OH, was dissolved in 3 mL of CH$_2$Cl$_2$, and cooled to 0° C. via ice bath. The clear, colorless reaction solution was then treated with 76 mg 1-hydroxybenzotriazole, 145 μL diisopropylethylamine, and 365 mg of the title compound from Step 11, Asp(OBz)-Pro-Thr(OBz)-allyl ester.HCl, while stirring. After all solids had dissolved, the reaction solution was treated with 108 mg of 1-(3-dimethylaminopropyl)-3-ethylcarbodiimide.HCl. After 4.5 hours, the CH$_2$Cl$_2$ was evaporated and replaced with ethyl acetate. The organic solution was washed with water, 1.5 M HCl and 5% NaHCO$_3$, dried over Na$_2$SO$_4$, and evaporated to a clear, colorless oil. The entire sample was chromatographed by flash column eluting with 5% MeOH/CHCl$_3$. The title compound (407 mg), (S)-CBA-Lys(Z)-Pec-Asp(OBn)-Pro-Thr(OBn)-allyl ester, was isolated as a clear, colorless oil (67.5% yield).

Step 15

(S)-CBA-Lys(Z)-Pec-Asp(OBn)-Pro-Thr(OBn)-OH 2.2 mg of palladium acetate were dissolved in 2 mL dry THF. This clear, light orange solution was then treated with 5 mg of triphenylphosphine. In a separate vial, 138 μL of triethylamine was diluted with 1 mL dry THF and treated with 29 μL of formic acid. This complex was then added to the reaction solution, which promptly turned a dark green color. Finally, the title compound from Step 14 (407 mg), (S)-CBA-Lys(Z)-Pec-Asp(OBn)-Pro-Thr(OBn)-allyl ester was dissolved in 10 mL dry THF and added to the reaction solution. The atmosphere within the reaction vessel was evacuated and replaced with a steady stream of nitrogen. Reaction progress was monitored by TLC. After 86 hours, the solution was filtered through celite, and the clear, pale yellow filtrate was thoroughly evaporated to a sticky foam. The entire sample was chromatographed on silica gel, eluting with 10% MeOH/CHCl$_3$ plus 0.5% HOAc. After purification and lyophilization, 208 mg of the title compound, (S)-CBA-Lys(Z)-Pec-Asp(OBn)-Pro-Thr(OBn)-OH was isolated as a white solid (52.8% yield).

Step 16

(S)-CBA-Lys(Z)-Pec-Asp(OBn)-Pro-Thr(OBn)-leucinol 60 mg of the title compound from Step 15, (S)-CBA-Lys(Z)-Pec-Asp(OBz)-Pro-Thr(OBz)-OH were dissolved in 2 mL of CH$_2$Cl$_2$, and cooled to 0° C. via ice water bath. The clear, colorless reaction solution was treated with 9 mg of 1-hydroxybenzotriazole, 22 μL of diisopropylethylamine, and 11 μL of commercially available leucinol, while stirring. After all solids had dissolved, the reaction was treated with 13 mg of 1-(3-dimethylaminopropyl)-3-ethylcarbodiimide. The reaction flask was then stoppered, sealed with parafilm, and placed in the refrigerator overnight. The CH$_2$Cl$_2$ was thoroughly evaporated and replaced with ethyl acetate. The organic portion was washed with water, 1.5 M HCl, and 5% Na$_2$CO$_3$, dried over Na$_2$SO$_4$, and evaporated to yield 48 mg of the title compound, (S)-CBA-Lys(Z)-Pec-Asp(OBz)-Pro-Thr(OBz)-leucinol as a white solid (73% yield).

EXAMPLE 1

(S)-CBA-Val-Pec-Asp-Pro-Thr-propylamide

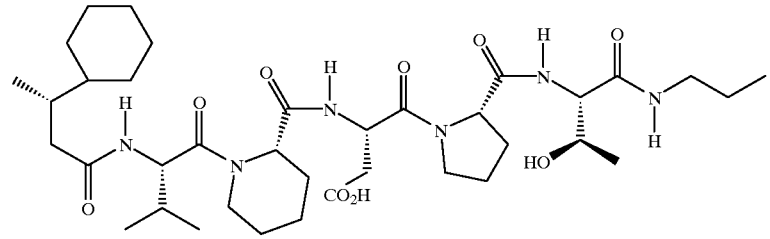

The title compound from Step 7 (62 mg of (S)-CBA-Val-Pec-Asp(OBz)-Pro-Thr(OBz)-propylamide) was mixed with 65 mg of 20% Pd(OH)2/C and 62 mg of 10% Pd/C in a 10 mL round bottom flask. This mixture was then treated with 0.5 mL of a 1.6M solution of NH$_4$HCO$_2$ in acetic acid, while stirring. The atmosphere in the reaction vessel was then evacuated and replaced with nitrogen. After 4 hours, the reaction was diluted with methanol and filtered through a celite plug to remove the catalyst. The resulting clear, colorless filtrate was thoroughly evaporated. The oily residue was dissolved in 3 mL distilled water and lyophilized. The title compound, was obtained (46 mg) as a fluffy, white solid (92%). Analysis by NMR (D$_2$O) verified that all protecting groups had been successfully removed. The title compound exhibited one single peak by HPLC. $^1$H NMR (400 MHz): consistent with proposed structure. Mass spectrum (m/e): 735.

EXAMPLE 2

(S)-CBA-Lys-Pec-Asp-Pro-Thr-propylamide

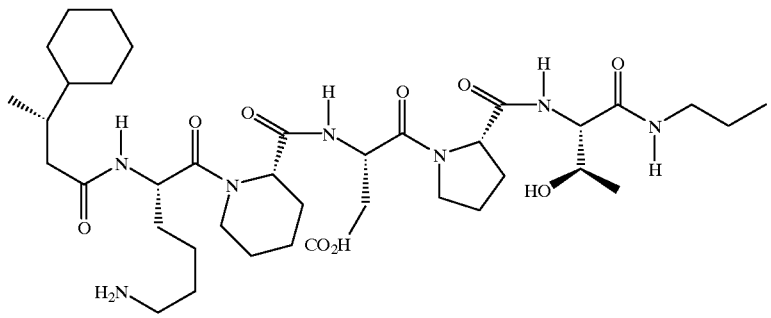

(S)-3-cyclohexylbutyroyl chloride (13 mg) was added to a two-phase mixture of water, ethyl acetate, the title compound of Step 4 (60 mg) and sodium bicarbonate (10 mg). After vigorously stirring for 30 minutes, the ethyl acetate phase was isolated and washed with 1N hydrochloric acid, then dried (magnesium sulfate) and the solvent evaporated. The residue was mixed with 65 mg of 20% Pd(OH)2/C and 62 mg of 10% Pd/C in a 10 mL round bottom flask. This mixture was then treated with 0.5 mL of a 1.6M solution of $NH_4HCO_2$ in acetic acid, while stirring, under nitrogen. After 4 hours, the reaction was diluted with methanol and filtered through a celite plug to remove the catalyst. The resulting clear, colorless filtrate was thoroughly evaporated. The oily residue was dissolved in 3 mL distilled water and lyophilized. The title compound was obtained (37 mg) as a fluffy, white solid (as the acetate salt). $^1$H NMR (400 MHz): consistent with proposed structure. Mass spectrum (m/e): 764.

EXAMPLE 3

CPA-Lys-Pec-Asp-Pro-Thr-propylamide

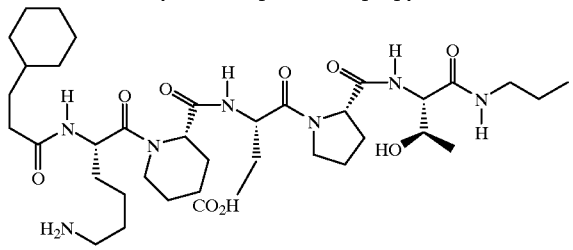

The same procedure of Example 2 was employed substituting cyclohexylpropionyl chloride in place of (S)-3-cyclohexylbutyroyl chloride gave the title compound (as the acetate salt). $^1$H NMR (400 MHz): consistent with proposed structure. Mass spectrum (m/e): 750.

EXAMPLE 4

(S)-CBA-Lys-Pec-Asp-Pro-Thr-leucinol

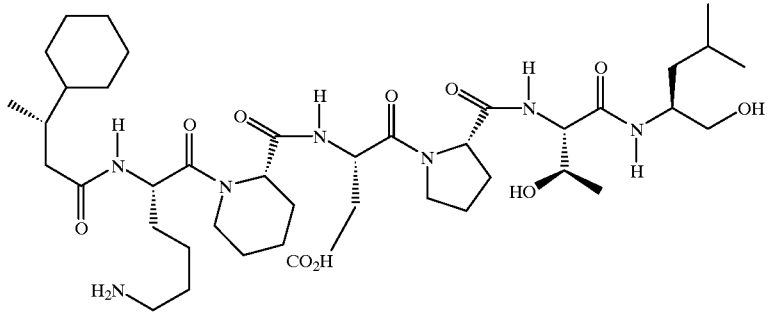

40 mg of the title compound of Step 16, (S)-CBA-Lys(Z)-Pec-Asp(OBn)-Pro-Thr(OBn)-leucinol, were combined with 45 mg of 20% Pd(OH)$_2$/C and 40 mg of 10% Pd/C in a 10 mL round bottom flask. This mixture was then treated with 0.5 mL of a 1.6 M solution of $NH_4HCO_2$ in HOAc, while stirring. The atmosphere in the reaction vessel was evacuated and replaced with a steady stream of $N_2$. After 4 hours, the reaction was diluted with MeOH and filtered through a celite plug to remove all catalyst. The clear, colorless filtrate was thoroughly evaporated. The oily residue was dissolved in 4 ml distilled water and lyophilized. 25 mg of the title compound (S)-CBA-Lys-Pec-Asp-Pro-Thr-leucinol was isolated as a fluffy, white solid (as the acetate salt, 86% yield). $^1$H NMR (400 MHz): consistent with proposed structure.

Compounds #5–#59, as shown in Table 1 below, may be synthesized by reference to the foregoing specific and general procedures for preparing compounds of Formula I.

TABLE I
| Example Compound No. | Structure |
|---|---|
| 5 | 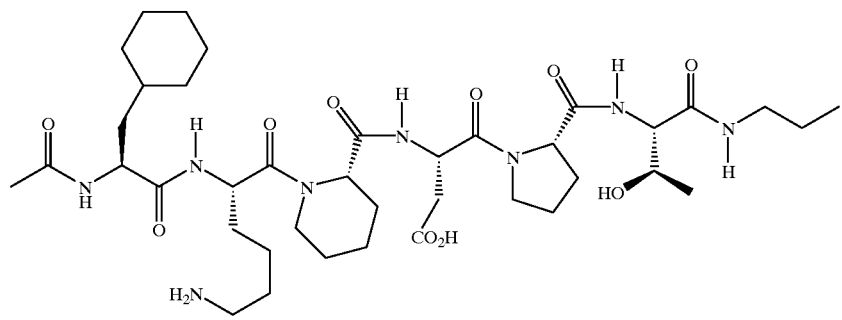 |
| 6 | 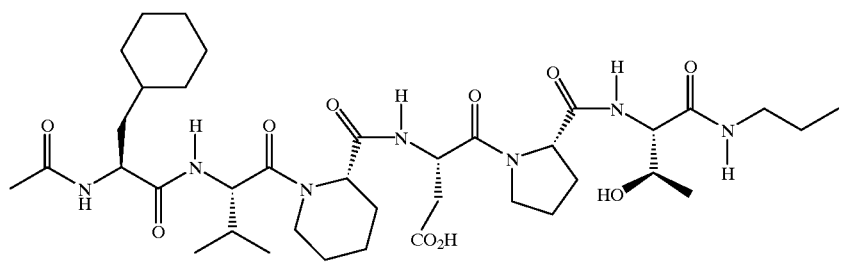 |
| 7 | 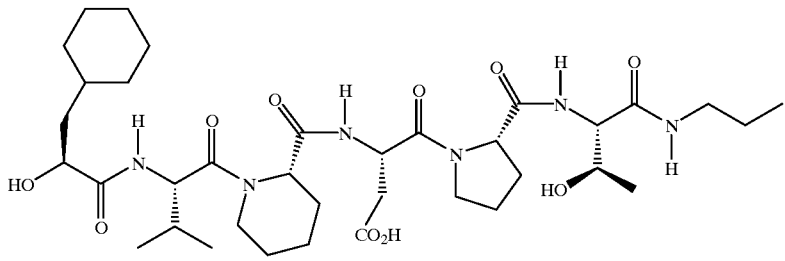 |
| 8 | 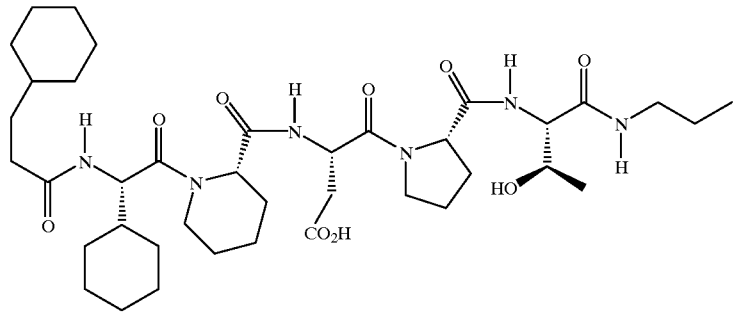 |
| 9 | 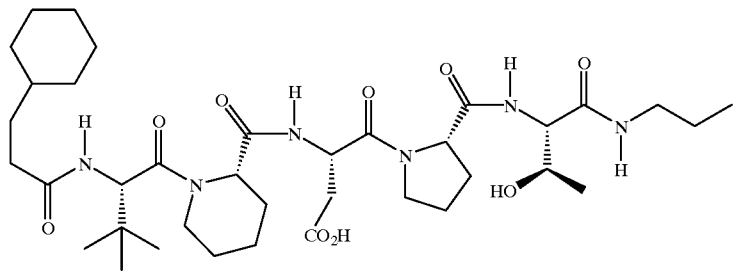 |

TABLE I-continued
| Example Compound No. | Structure |
|---|---|
| 10 | 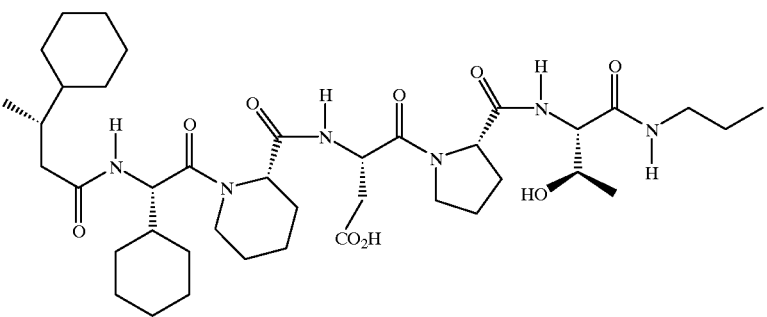 |
| 11 | 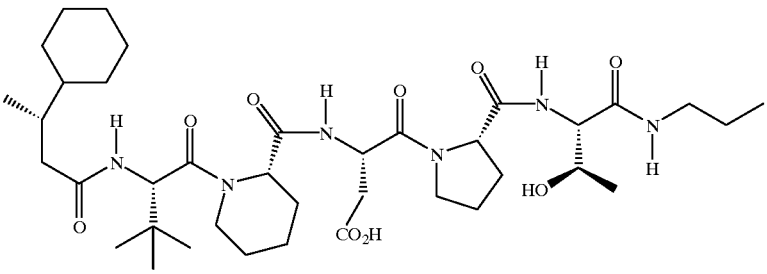 |
| 12 | 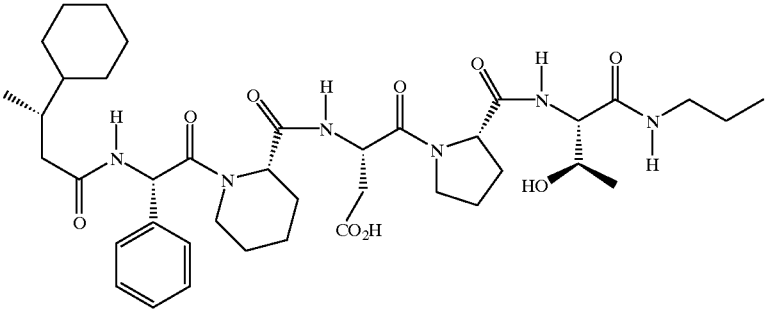 |
| 13 | 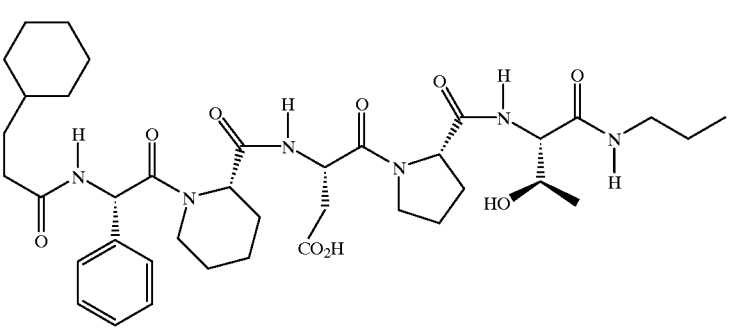 |

TABLE I-continued
Example
Compound No. Structure
14
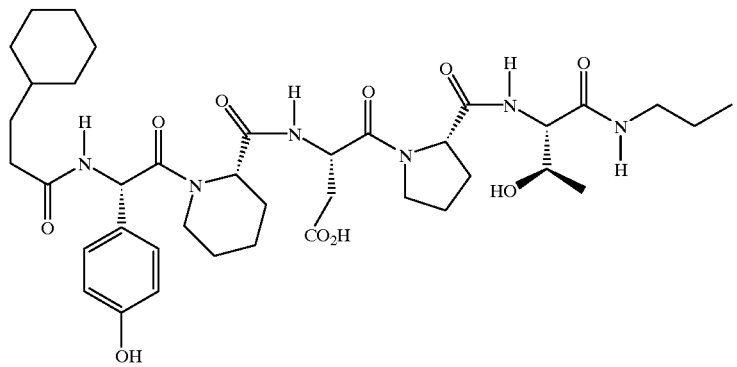
15
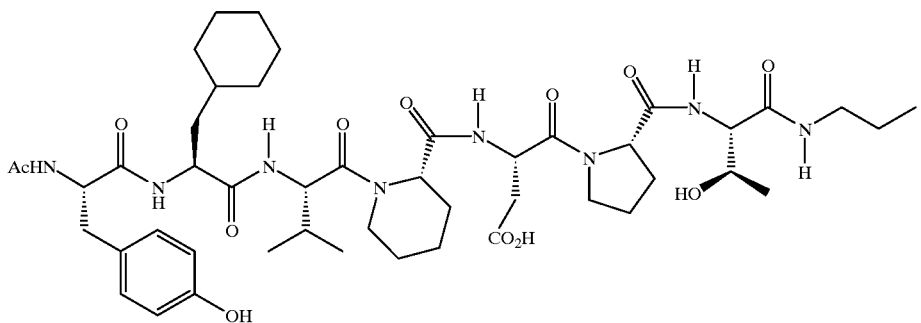
16
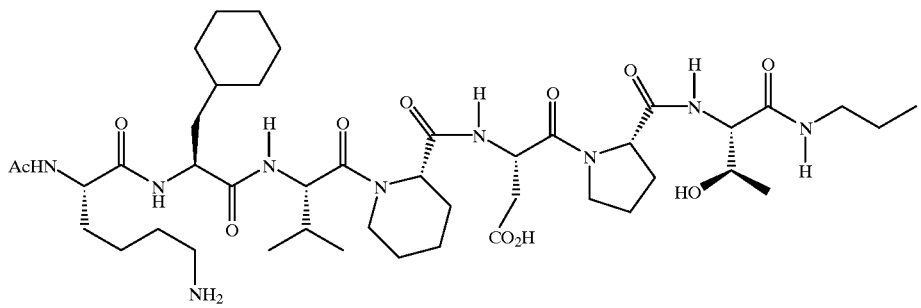
17
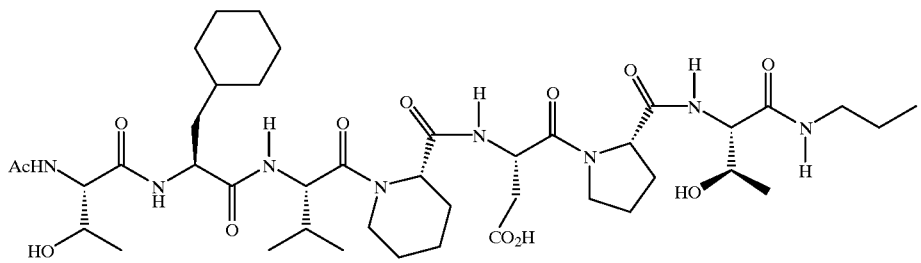

TABLE I-continued
| Example Compound No. | Structure |
|---|---|
| 18 | 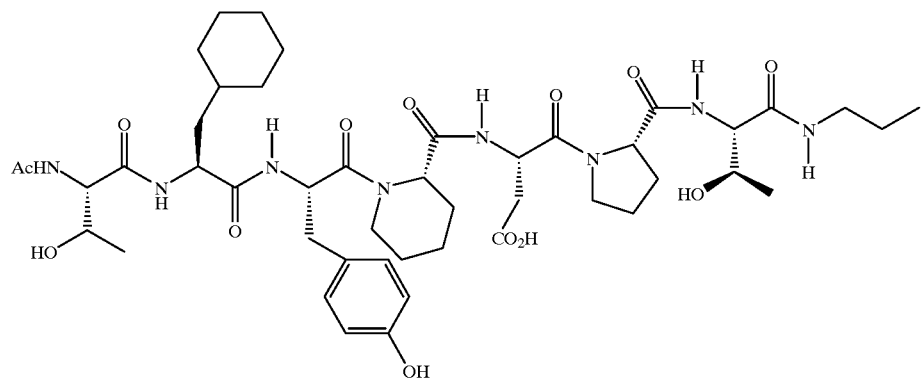 |
| 19 | 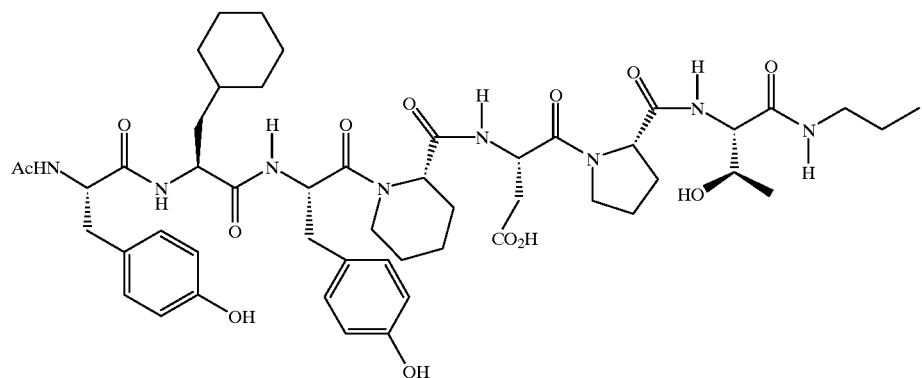 |
| 20 | 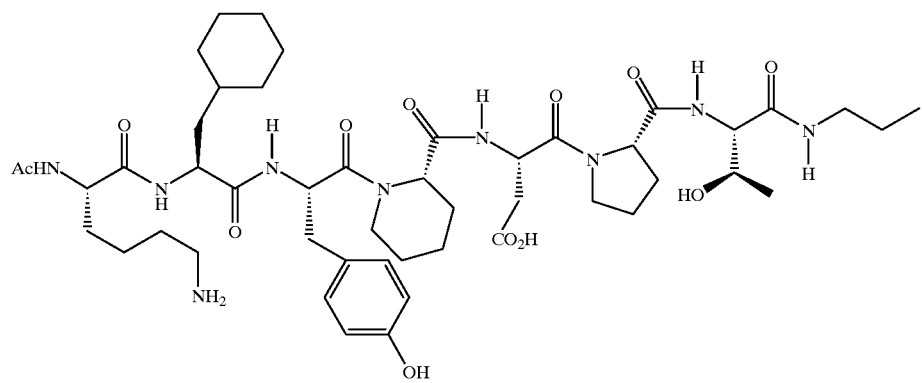 |
| 20 | 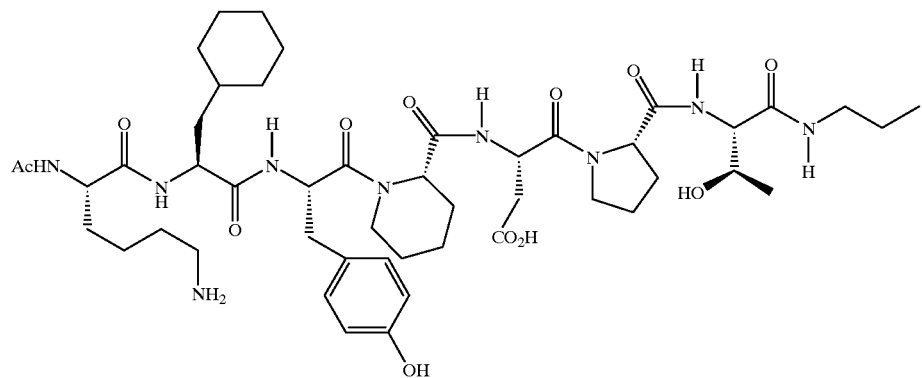 |

TABLE I-continued
Example
Compound No. Structure
21
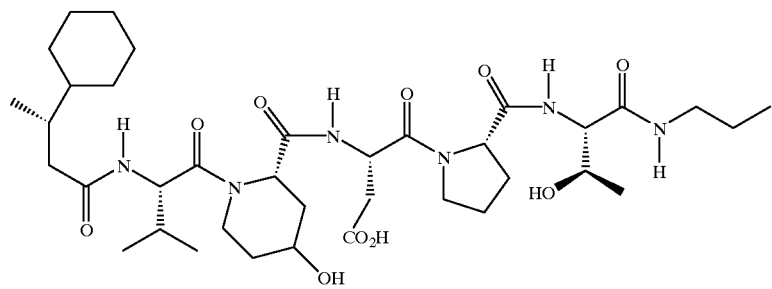
22
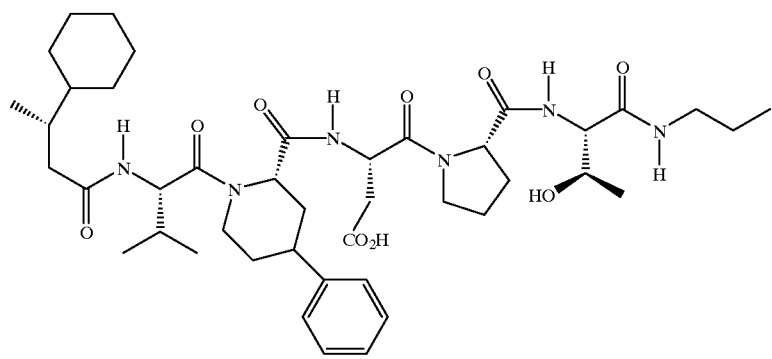
23
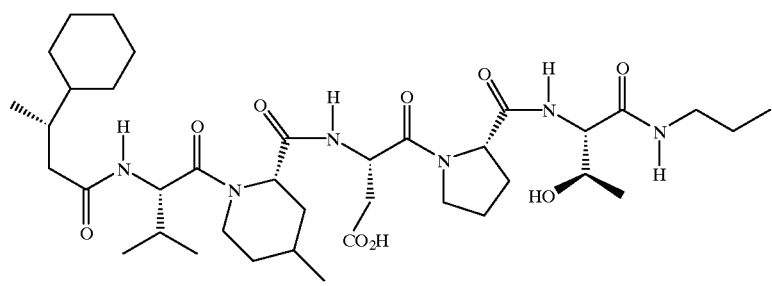
24
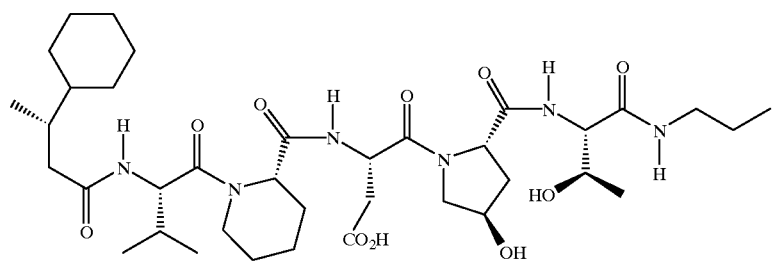
25
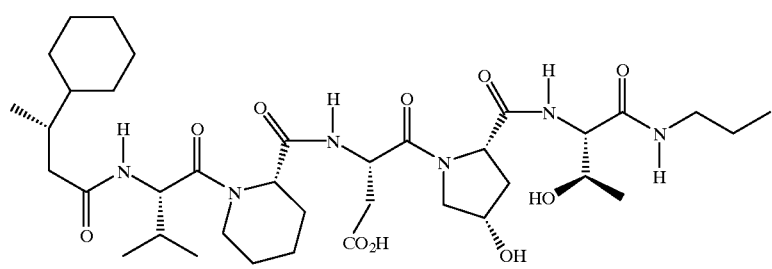

TABLE I-continued

| Example Compound No. | Structure |
|---|---|
| 26 | 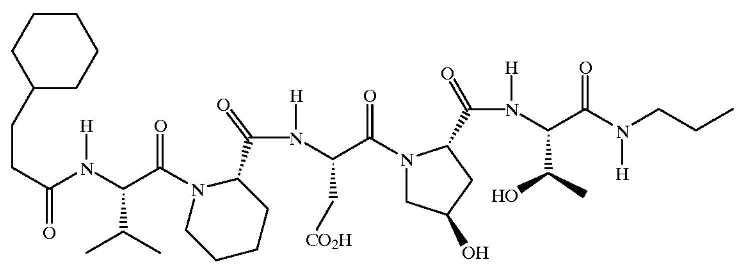 |
| 27 | 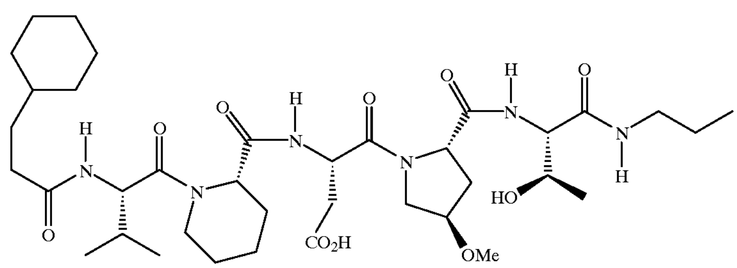 |
| 28 | 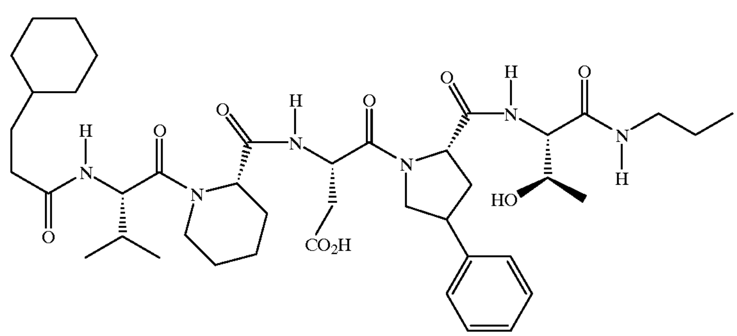 |
| 29 | 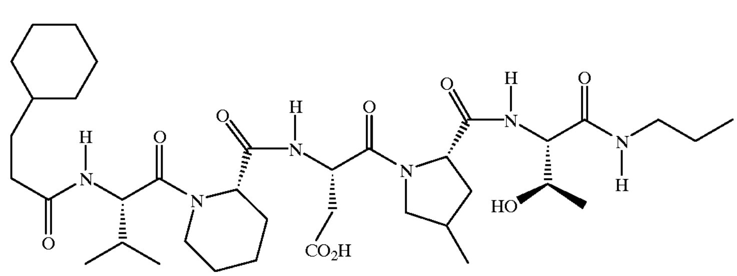 |
| 30 | 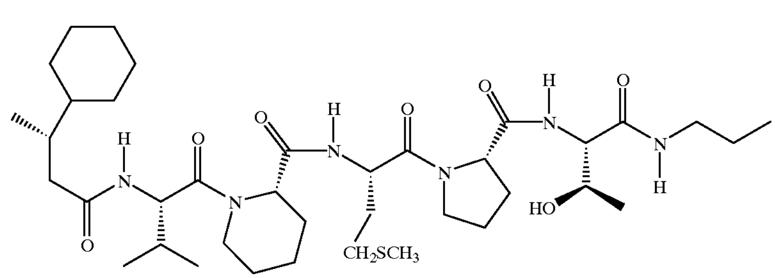 |

TABLE I-continued
| Example Compound No. | Structure |
|---|---|
| 31 | 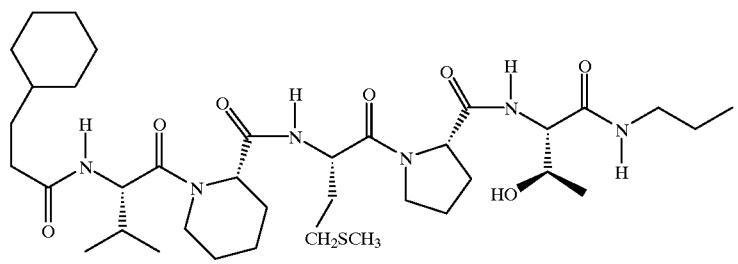 |
| 32 | 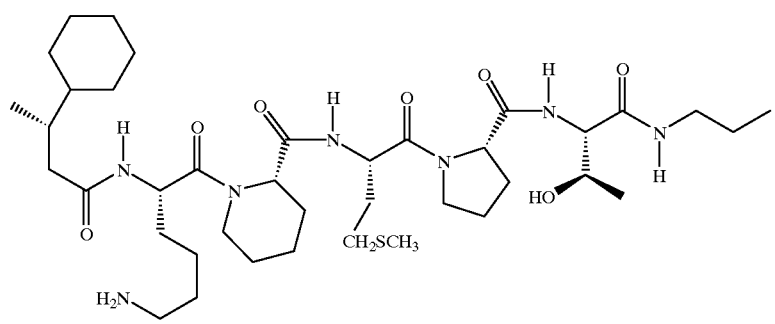 |
| 33 | 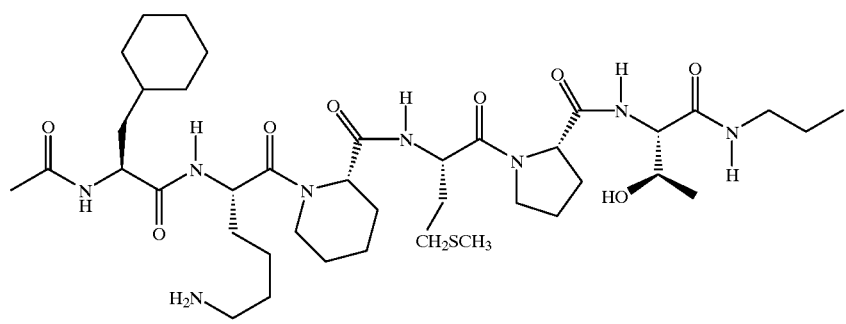 |
| 34 | 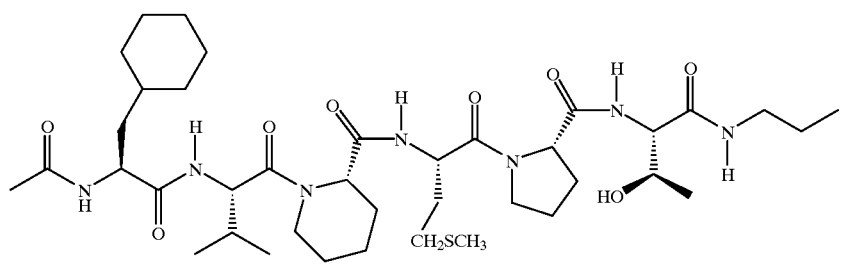 |
| 35 | 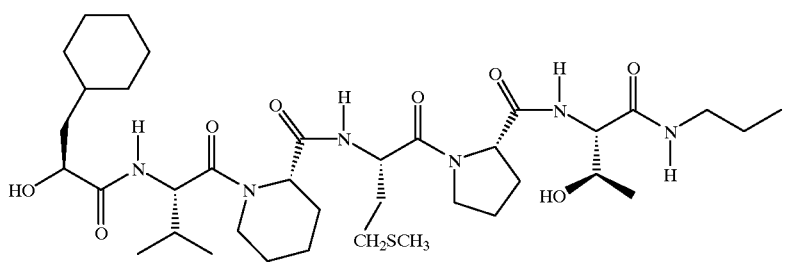 |

TABLE I-continued
| Example Compound No. | Structure |
|---|---|
| 36 | 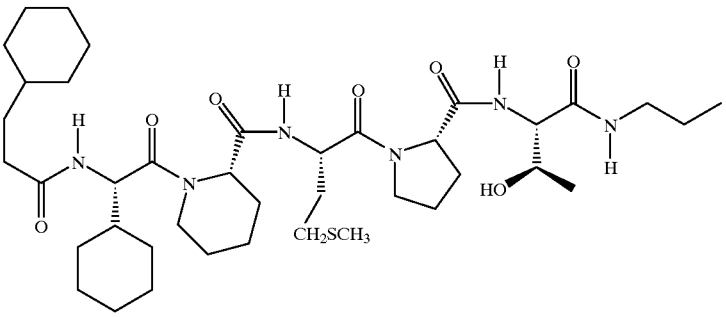 |
| 37 | 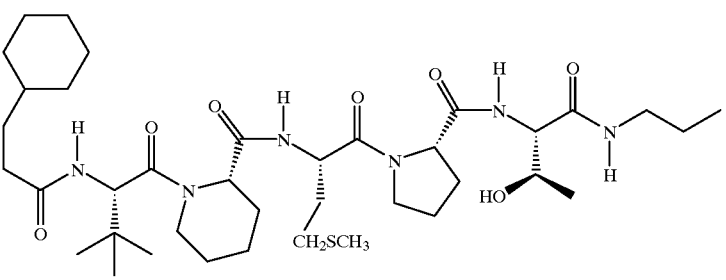 |
| 38 | 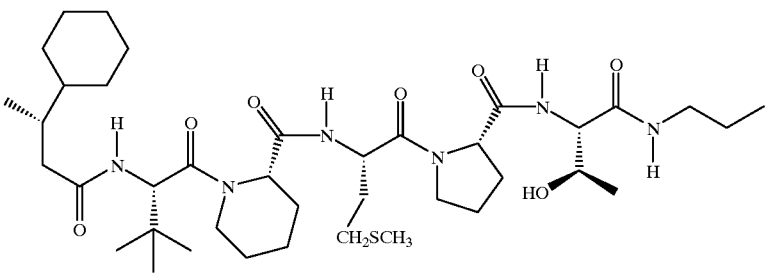 |
| 39 | 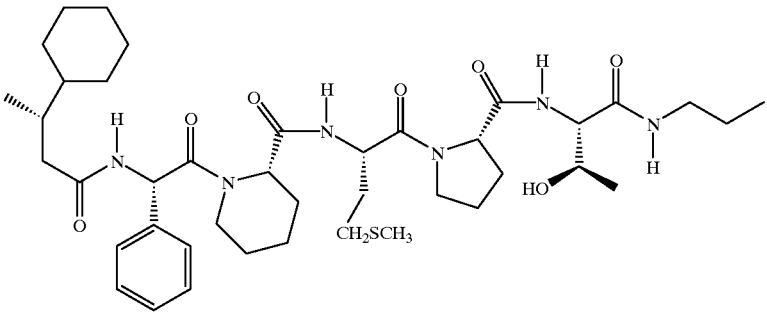 |

TABLE I-continued

| Example Compound No. | Structure |
|---|---|
| 40 | 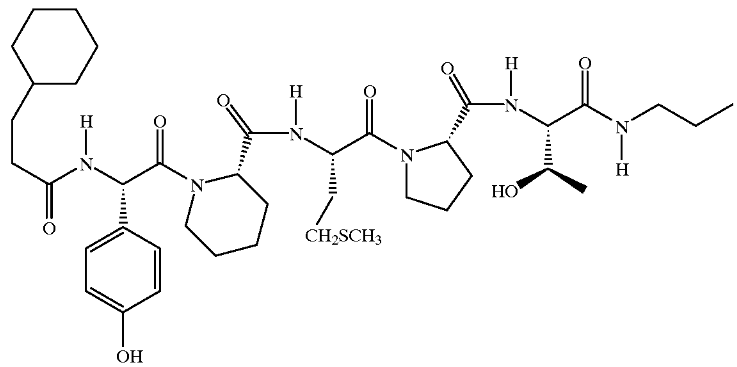 |
| 41 | 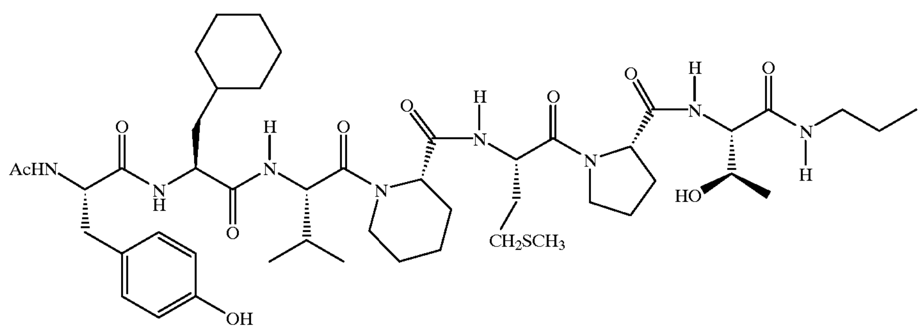 |
| 42 | 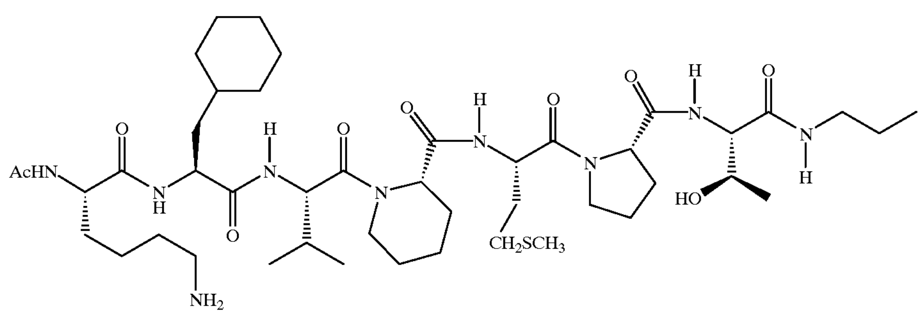 |
| 43 | 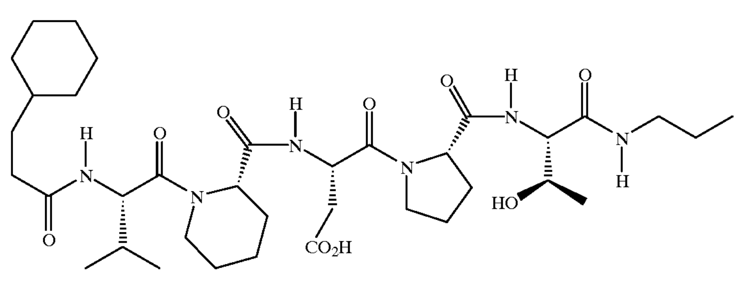 |

TABLE I-continued
| Example Compound No. | Structure |
|---|---|
| 44 | 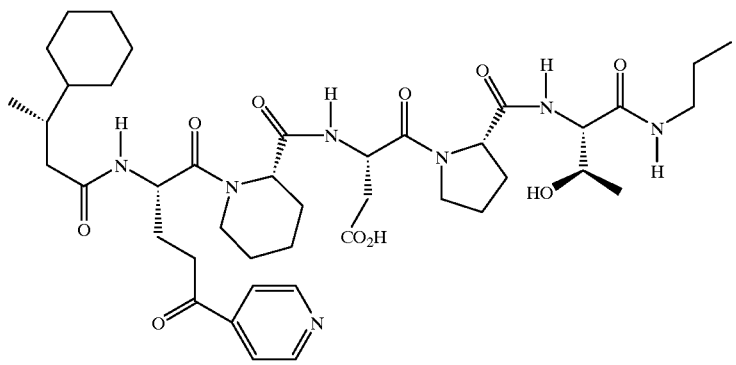 |
| 45 | 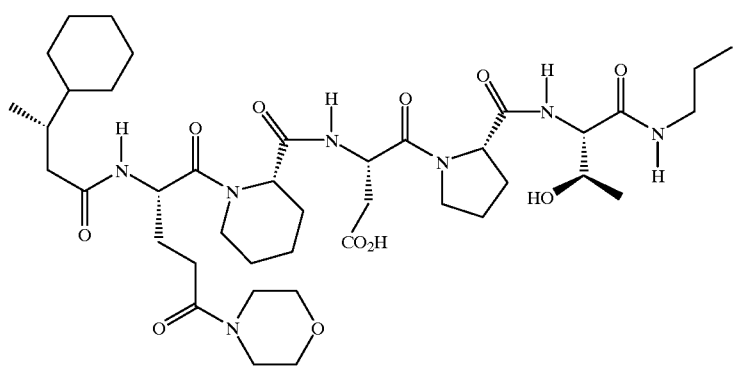 |
| 46 | 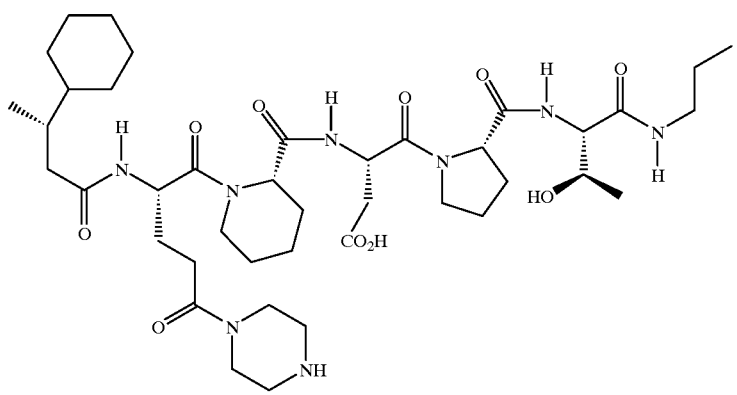 |
| 47 | 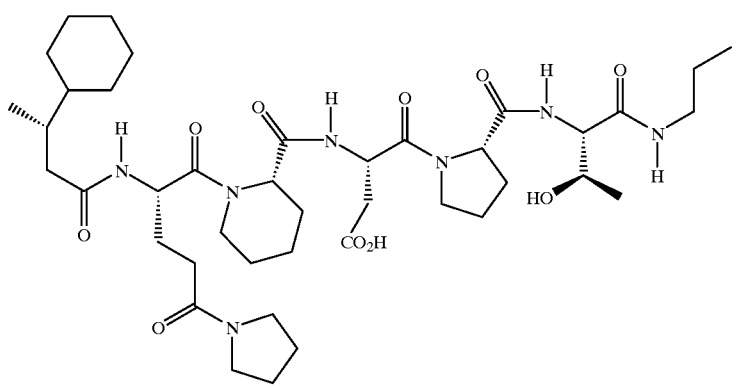 |

TABLE I-continued
| Example Compound No. | Structure |
|---|---|
| 48 | 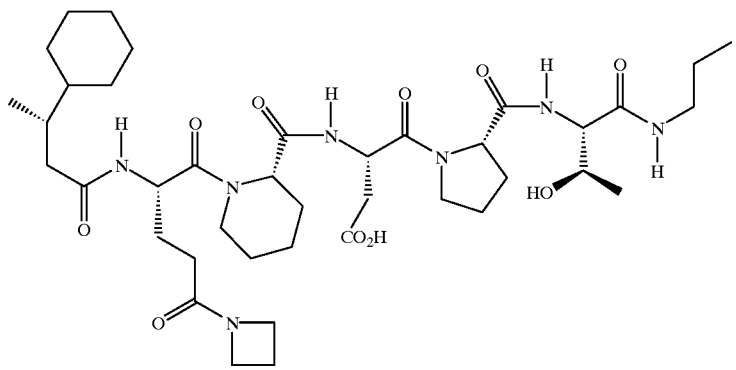 |
| 49 | 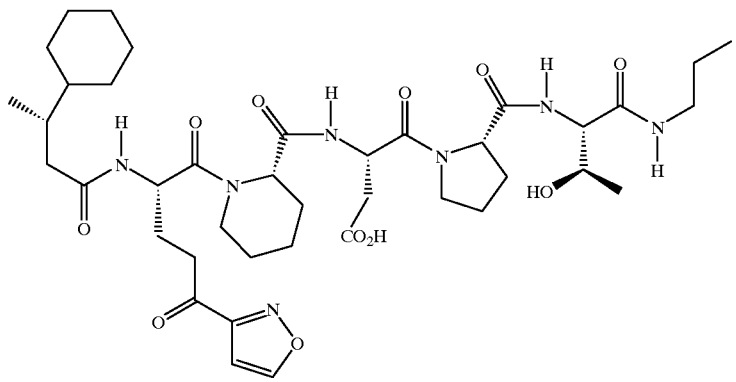 |
| 50 | 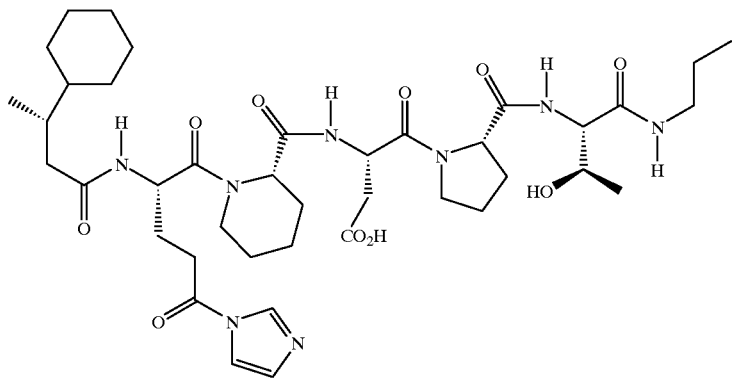 |
| 51 | 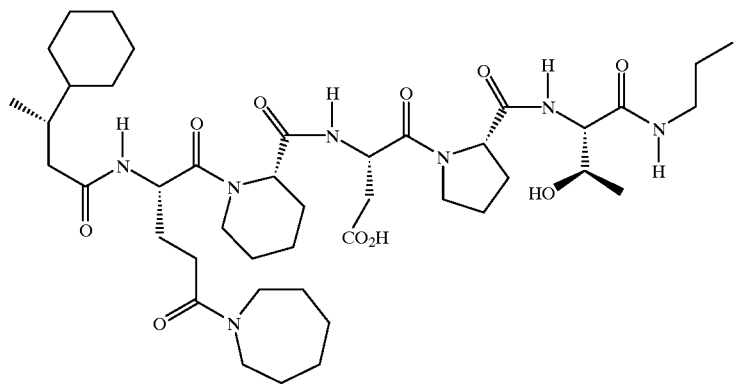 |

TABLE I-continued
Example
Compound No. Structure
52
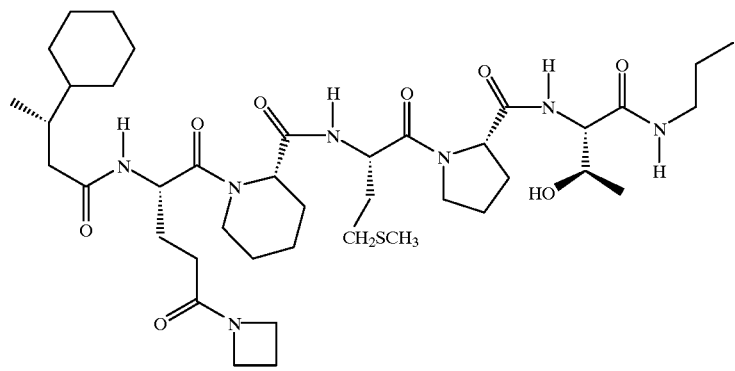
53
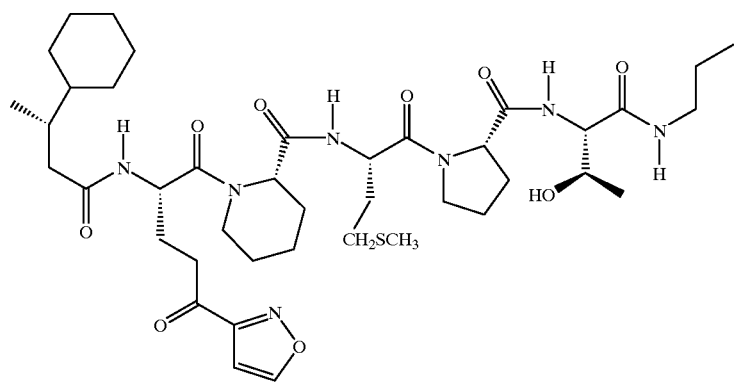
54
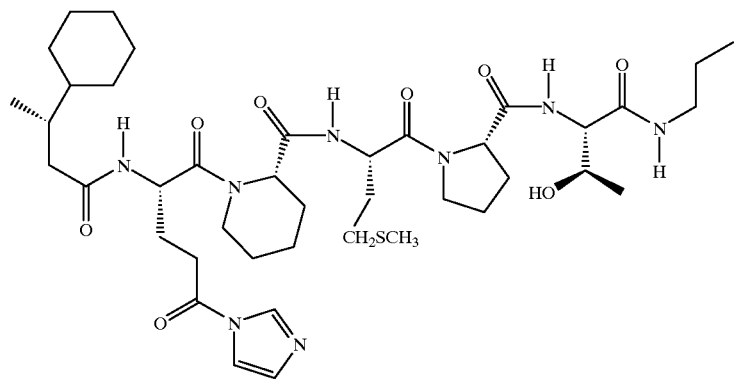

TABLE I-continued
Example
Compound No. Structure
55
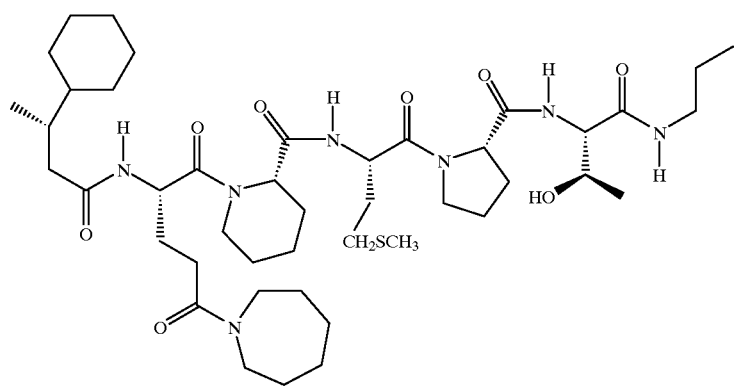
56
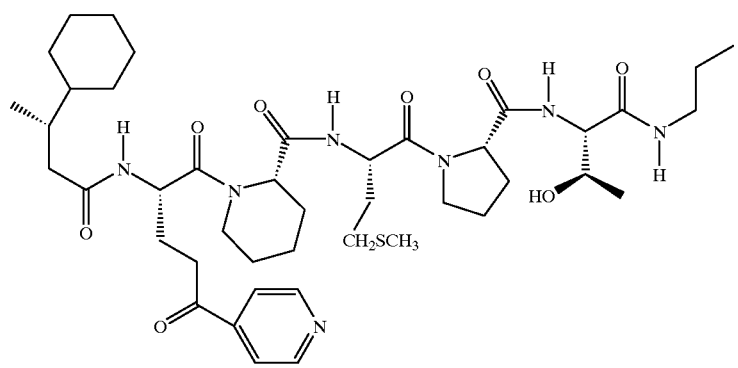
57
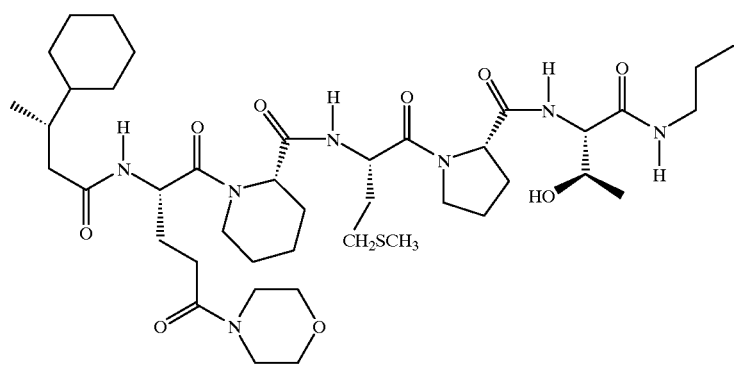
58
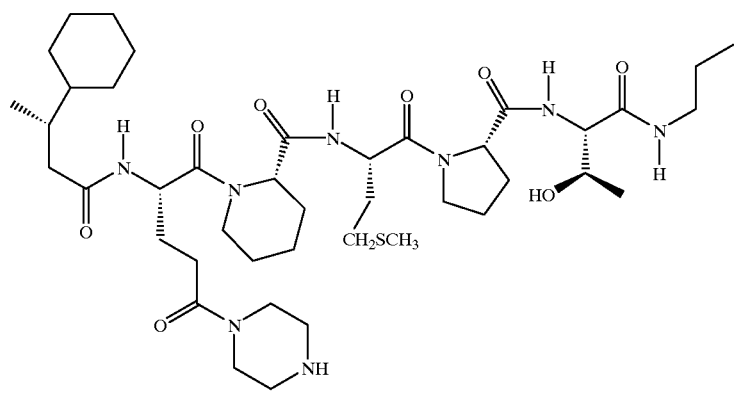

TABLE I-continued

Example
Compound No. Structure

59

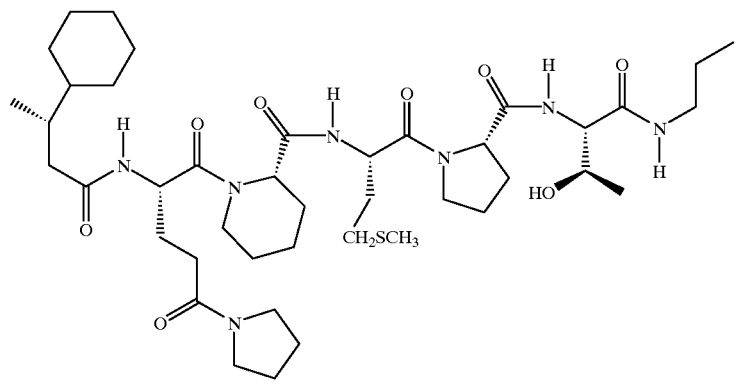

Biological Evaluation

Competitive Binding for DR4 (Competition Capture ELISA)

DR(αβ1*0401) molecules are affinity purified with L243 monoclonal antibody (hybridoma obtained from ATCC) using a modification of a published procedure (Gorga, J. C., et al., 1991. Res. Immunol. 142:401–407.). Duplicate samples of immunoaffinity purified DRB1*0401 molecules (0.5 μg/well) are incubated overnight at 37° C. with 50 nM biotinylated ML37-49 peptide in the presence or absence of 1 nM to 100 μM competitor peptides in 96-well polypropylene microtiter plates (Costar, Cambridge, Mass.). All dilutions are made in phosphate buffered saline, pH 5.5 containing 1% octaglucoside (Boehringher Mannheim). LB3.1 antibody (obtained from J. Strominger, Cambridge, Mass.) is plated onto flat-bottom 96-well polystyrene microtiter plates (Falcon, Becton-Dickinson, Mountainview, Calif.) in 0.1 M carbonate coating buffer, pH 9.6 overnight at 4° C. Antibody coated microtiter plates are blocked with 1% Carnation nonfat milk for 1 hr at room temperature. The plates are washed 3 times with PBS containing 0.05% Tween 20 (Biorad, Hercules, Calif.). The class II/peptide mixtures are added, incubated for 1 hr at 37° C., and washed as described above. Extravidin conjugated horseradish peroxidase (1:1000, Sigma Chemicals) is added to the wells and incubated for 30–60 min at 37° C. The plates are washed again, then incubated with o-phenylenediamine dihydrochloride and $H_2O_2$ (Sigma Chemicals, St. Louis, Mo.) in 0.5 M phosphate-citrate buffer, pH 5.0. The absorbance of each well is read at 450 nm.

TABLE II

| Competition Capture ELISA | |
|---|---|
| Example no. | IC50 (nM) |
| 1 | 30 |
| 2 | 289 |
| 3 | 259 |
| 4 | 116 |

Inhibition of T cell Proliferation Assay

Triplicate wells containing 2×104 DR4 Dw4 positive antigen presenting cells (APC) are incubated in Excell 300 serum-free media containing 2 mM glutamine and 1% penicillin-streptomycin solution or in RPMI1640 containing 10% pooled human serum, 2 mM glutamine and 1% penicillin-streptomycin solution (R-10). The APC may be B-lymphoblastoid cells, L cells transfected with DR4Dw4, or peripheral blood lymphocytes. The APC are incubated under serum-containing or serum-free conditions with varying concentrations (0.01–500 μM) of competitor peptides for 2–4 hr at 37° C., 5% $CO_2$. Suboptimal concentrations of HA307-319 peptide (0.01 to 1 μM) or hemagglutinin protein are added to the wells at the same time as the competitor peptides (co-incubation) for 4 hr or for 2 hr following 2 hr of incubation with the competitor peptides (competitor prepulse). The plates are washed with the appropriate media three times to remove unbound peptides. The remainder of the assay is done in R-10. 4×104 clonal human DR4 Dw4-restricted HA-specific T cells are added to the wells and incubated 3 days at 37° C., 5% CO2. PHA (5 μg/ml) is added to some of the wells in the presense or absence of competitor peptides to determine if the peptides are cytotoxic. 3H-thymidine (0.5 μCi/well) is added to the cultures, incubated an additional 18 hr, and incorporation of radiolabel is determined using a β-scintillation counter. Compounds of the invention are active in inhibiting the proliferation of T-cells in this assay.

Administration of the compounds of Formula I may be accomplished by administering a formulation containing an active compound by oral route, or by intravenous, intramuscular or subcutaneous injections. The formulation may be in the form of a bolus, or in the form of aqueous or non-aqueous isotonic sterile injection solutions or suspensions. These solutions and suspensions may be prepared from sterile powders or granules having one or more pharmaceutically-acceptable carriers or diluents, or a binder such as gelatin or hydroxypropyl-methyl cellulose, together with one or more of a lubricant, preservative, surface-active or dispersing agent.

For oral administration, the pharmaceutical composition may be in the form of, for example, a tablet, capsule, suspension or liquid. The pharmaceutical composition is preferably made in the form of a dosage unit containing a particular amount of the active ingredient. Examples of such dosage units are tablets or capsules. These may with advantage contain an amount of each active ingredient from about 1 to 250 mg, preferably from about 25 to 150 mg. A suitable daily dose for a mammal may vary widely depending on the condition of the patient and other factors. However, a dose of from about 0.1 to 3000 mg/kg body weight, particularly from about 1 to 100 mg/kg body weight, may be appropriate.

The active ingredients may also be administered by injection as a composition wherein, for example, saline, dextrose or water may be used as a suitable carrier. A suitable daily dose of each active component is from about 0.1 to 100 mg/kg body weight injected per day in multiple doses depending on the disease being treated. A preferred daily dose would be from about 1 to 30 mg/kg body weight. Compounds indicated for prophylactic therapy will preferably be administered in a daily dose generally in a range from about 0.1 mg to about 100 mg per kilogram of body weight per day. A more preferred dosage will be a range from about 1 mg to about 100 mg per kilogram of body weight. Most preferred is a dosage in a range from about 1 to about 50 mg per kilogram of body weight per day. A suitable dose can be administered, in multiple sub-doses per day. These sub-doses may be administered in unit dosage forms. Typically, a dose or sub-dose may contain from about 1 mg to about 100 mg of active compound per unit dosage form. A more preferred dosage will contain from about 2 mg to about 50 mg of active compound per unit dosage form. Most preferred is a dosage form containing from about 3 mg to about 25 mg of active compound per unit dose.

The dosage regimen for treating a disease condition with the combination therapy of this invention is selected in accordance with a variety of factors, including the type, age, weight, sex and medical condition of the patient, the severity of the disease, the route of administration, and the particular compound employed, and thus may vary widely.

For therapeutic purposes, the active component of this invention is ordinarily combined with one or more adjuvants appropriate to the indicated route of administration. If administered per os, the components may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets may contain a controlled-release formulation as may be provided in a dispersion of active compound in hydroxypropylmethyl cellulose. Formulations for parenteral administration may be in the form of aqueous or non-aqueous isotonic sterile injection solutions or suspensions These solutions and suspensions may be prepared from sterile powders or granules having one or more of the carriers or diluents mentioned for use in the formulations for oral administration. The components may be dissolved in water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art.

Although this invention has been described with respect to specific embodiments, the details of these embodiments are not to be construed as limitations.

What is claimed is:

1. A compound of Formula I:

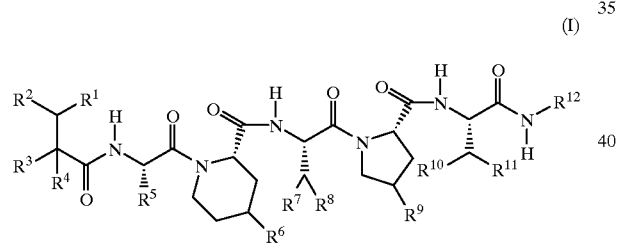

(I)

wherein $R^1$ is selected from alkyl, phenyl, cycloalkyl rings having four to ten ring-member carbon atoms, bicycloalkyl fused ring systems having seven to nine ring-member carbon atoms, heteroaryl, heteroarylalkyl, benzo-fused-heteroaryl and benzo-fused-heteroarylalkyl wherein said heteroaryl moiety or fragment is a 5- or 6-ring-member fully-unsaturated ring system having one hetero atom as a ring member, said hetero atom selected from oxygen, nitrogen and sulfur atoms, and wherein any of said heteroaryl, heteroarylalkyl, benzo-fused-heteroaryl and benzo-fused-heteroarylalkyl may be attached to the nucleus of Formula I as an $R^1$ substituent through a bond formed at any said ring-member atom or any atom of the alkyl portion of said $R^1$ substituent where said bond is capable of forming a stable compound;

wherein $R^2$ is selected from hydrido, lower alkyl, cyclohexyl and phenyl;

wherein $R^3$ is selected from hydrido, hydroxy, lower alkyl, phenyl, acetyl(Lys)NH—, acetyl(Tyr)NH—, acetyl(Thr)NH—, acetylamino, propionylamino and benzyloxycarbonylamino;

wherein $R^4$ is selected from hydrido, lower alkyl and phenyl;

wherein $R^5$ is selected from hydrido, lower alkyl, phenyl, benzyl, hydroxyphenyl, hydroxybenzyl, aminoalkyl, mono-alkyl-substituted-aminoalkyl and radicals provided by B-Het-A;

wherein Het is selected from heteroaryl moieties consisting of monocyclic and fused bicyclic ring systems having a total of five to fourteen ring members and with one to six ring members being selected from hetero atoms provided by oxygen, nitrogen and sulfur atoms, wherein said monocyclic ring system and at least one ring system of said fused bicyclic ring system is fully unsaturated, and wherein Het is further selected from heterocyclic moieties consisting of monocyclic and fused polycyclic ring systems having a total of four to twelve ring members and with one to six ring members selected from hetero atoms provided by oxygen, nitrogen and sulfur atoms, wherein said monocyclic ring-system and at least one ring system of said fused polycyclic ring system is fully saturated or partially unsaturated, wherein A is a single covalent bond or is a divalent radical selected from

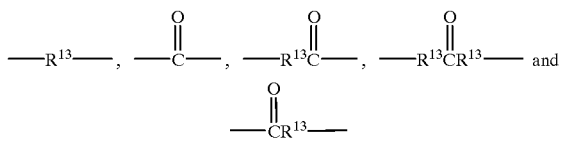

wherein $R^{13}$ is lower alkyl;

wherein B is one or more substituents attached at a substitutable position on Het of Het-A, said substituent selected from hydrido, hydroxy, alkyl, cycloalkyl, cycloalkylalkyl, alkoxy, hydroxyalkyl, alkoxyalkyl, carboxy, alkenyl, alkynyl, halo, haloalkyl, oxo, cyano, benzyl and phenyl;

wherein $R^6$ is selected from hydrido, lower alkyl, hydroxy, alkoxy, alkoxyalkyl, carboxyalkyl, alkoxycarbonyl, alkoxycarbonyloxy, aminoalkyl, mono-alkyl-substituted-aminoalkyl, amido and amidoalkyl;

wherein $R^7$ is selected from carboxyl, lower alkyl, amido and methylthiomethyl;

wherein $R^8$ is selected from hydrido, methyl and ethyl;

wherein $R^9$ is selected from hydrido, lower alkyl, alkoxy and phenyl;

wherein $R^{10}$ is hydrido or hydroxy;

wherein $R^{11}$ is hydrido or methyl;

wherein $R^{12}$ is selected from lower alkyl, phenyl, phenylalkyl, cycloalkyl, cycloalkylalkyl,

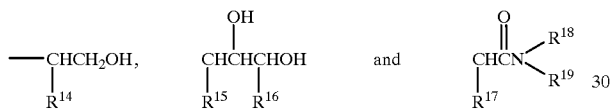

wherein each of $R^{14}$ through $R^{17}$ is independently selected from hydrido, hydroxy, alkyl, hydroxyalkyl, alkoxy, alkoxyalkyl, cycloalkyl, cycloalkylalkyl, halo, haloalkyl, cyano, benzyl and phenyl;

wherein each of $R^{18}$ and $R^{19}$ is independently selected from hydrido, alkyl, cycloalkyl, cycloalkylalkyl, benzyl and phenyl;

or a pharmaceutically-acceptable amide, ester or salt thereof.

2. A compound of claim 1 wherein $R^1$ is selected from cyclopentyl, cyclohexyl, cycloheptyl, norbornanyl, phenyl, furyl, pyrrolyl, thienyl, chromanyl, isochromanyl, benzothienyl, pyridyl, indolizinyl, isoindolyl, indolyl, 3H-indolyl, quinolizinyl, quinolyl, isoquinolyl, azetidinyl, thioazetidinyl, pyrrolidinyl, pyrrolinyl, oxazolidinyl, thiazolidinyl, imidazolidinyl, imidazolinyl, pyrazolidinyl, pyrazolinyl, piperidinyl, piperazinyl, 1,3-morpholino, 1,4-morpholino, 1,4-thiomorpholino, azepinyl, oxazopinyl, thiazopinyl, oxazocinyl, thiazocinyl, azoninyl, oxazabicyclo, benzo-fused-oxazolidinyl, benzo-fused-thiazolidinyl, benzo-fused-morpholino, benzo-fused thiomorpholinyl, benzo-fused-thiazopinyl, benzo-fused oxazopinyl, benzo-fused-oxazocinyl, benzo-fused-oxazoninyl, tropanyl and benzo-fused-oxazobicyclo;

wherein $R^2$ is selected from hydrido, methyl, ethyl, propyl, cyclohexyl and phenyl;

wherein $R^3$ is selected from hydrido, hydroxy, methyl, ethyl, phenyl, acetyl (Lys)NH—, acetyl (Tyr)NH—, acetyl (Thr)NH—, acetylamino, propionylamino and benzyloxycarbonylamino;

wherein $R^4$ is hydrido or methyl;

wherein $R^5$ is selected from hydrido, n-propyl, isopropyl, n-butyl, isobutyl, phenyl, benzyl, hydroxyphenyl, hydroxybenzyl, aminopropyl, aminobutyl and radicals provided by B-Het-$R^{13}$ and

wherein Het is selected from furyl, pyrrolyl, thienyl, chromanyl, isochromanyl, benzothienyl, pyridyl, indolizinyl, isoindolyl, indolyl, 3H-indolyl, quinolizinyl, quinolyl, isoquinolyl, imidazolyl, pyrazolyl, oxazolidyl, thiazolidyl, isothiazolidyl, isoxazolidyl, furazanyl, pyrazinyl, pyrimidinyl, pyridazinyl, indazolyl, purinyl, phthalazinyl, naphthyridinyl, quinoxalinyl, quinazolinyl, cinnolinyl, pteridinyl, thieno-furanyl, furopyranyl, pyrido-oxazinyl, pyrazolo-oxazolyl, imidazo-thiazolyl, pyrazino-pyridazinyl, imidazo-thiazolyl, oxothiolo-pyrrolyl, imidazo-triazinyl, benzoxazinyl, azetidinyl, thioazetidinyl, pyrrolidinyl, pyrrolinyl, oxazolidinyl, thiazolidinyl, imidazolidinyl, imidazolinyl, pyrazolidinyl, pyrazolinyl, piperidinyl, piperazinyl, 1,3-morpholino, 1,4-morpholino, 1,4-thiomorpholino, azepinyl, oxazopinyl, thiazopinyl, oxazocinyl, thiazocinyl, azoninyl, oxazabicyclo, benzo-fused-oxazolidinyl, benzo-fused-thiazolidinyl, benzo-fused-morpholino, benzo-fused thiomorpholinyl, benzo-fused-thiazopinyl, benzo-fused oxazopinyl, benzo-fused-oxazocinyl, benzo-fused-oxazoninyl, tropanyl and benzo-fused-oxazobicyclo;

wherein $R^{13}$ is lower alkyl;

wherein B is one or more substituents attached at a substitutable position on Het, said substituent selected from hydrido, hydroxy, alkyl, cycloalkyl, cycloalkylalkyl, alkoxy, hydroxyalkyl, alkoxyalkyl, oxo, benzyl and phenyl;

wherein $R^6$ is selected from hydrido, lower alkyl, hydroxy, methoxy carboxyalkyl, alkoxycarbonyl, alkoxycarbonyloxy, aminoalkyl, mono-alkyl-substituted-aminoalkyl, amido and amidoalkyl;

wherein $R^7$ is selected from carboxyl, lower alkyl, amido and methylthiomethyl;

wherein $R^8$ is hydrido or methyl;

wherein $R^9$ is selected from hydrido, lower alkyl, methoxy and phenyl;

wherein $R^{10}$ is hydrido or hydroxy;

wherein $R^{11}$ is hydrido or methyl;

wherein $R^{12}$ is selected from lower alkyl, phenyl, benzyl, phenylethyl,cyclohexylethyl,

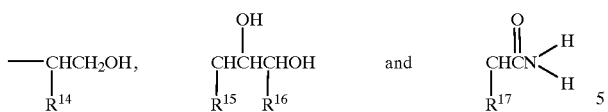

wherein each of $R^{14}$ through $R^{17}$ is independently selected from hydrido, hydroxy and alkyl;
or a pharmaceutically-acceptable amide, ester or salt thereof.

3. A compound of claim 2 wherein $R^1$ is selected from cyclopentyl, cyclohexyl, cycloheptyl, norbornanyl, phenyl, azetidinyl, thioazetidinyl, pyrrolidinyl, pyrrolinyl, oxazolidinyl, thiazolidinyl, imidazolidinyl, imidazolinyl, pyrazolidinyl, pyrazolinyl, piperidinyl, piperazinyl 1,3-morpholino, 1,4-morpholino, 1,4-thiomorpholino, azepinyl, oxazopinyl, thiazopinyl, oxazocinyl, thiazocinyl, azoninyl, oxazabicyclo and tropanyl;
wherein $R^2$ is selected from hydrido, methyl, ethyl, propyl, acetyl (Lys)NH—, acetyl (Tyr)NH—, acetyl (Thr)NH—, cyclohexyl and phenyl;
wherein $R^3$ is selected from hydrido, hydroxy, methyl, ethyl, phenyl, acetylamino, propionylamino and benzyloxycarbonylamino;
wherein $R^4$ is hydrido or methyl;
wherein $R^5$ is selected from hydrido, n-propyl, isopropyl, n-butyl, isobutyl, aminopropyl, aminobutyl, phenyl, hydroxyphenyl, benzyl, hydroxybenzyl and radicals provided by

wherein Het is selected from azetidinyl, pyridinyl, isoindolyl, oxazolyl, isoxazolyl, indolyl, quinolyl, isoquinolyl, azetidinyl, thioazetidinyl, pyrrolidinyl, pyrrolinyl, oxazolidinyl, thiazolidinyl, imidazolyl, imidazolidinyl, imidazolinyl, pyrazolidinyl, pyrazolinyl, piperidinyl, piperazinyl, 1,3-morpholino, 1,4-morpholino, 1,4-thiomorpholino, azepinyl, oxazopinyl, thiazopinyl, oxazocinyl, thiazocinyl, azoninyl, oxazabicyclo and tropanyl;
wherein $R^{13}$ is selected from methyl, ethyl and propyl;
wherein B is one or more substituents attached at a substitutable position on Het, said substituent selected from hydrido, hydroxy, methyl, ethyl, propyl, oxo, benzyl and phenyl;
wherein $R^6$ is selected from hydrido, methyl, hydroxy, methoxy, phenyl, alkoxycarbonyl, alkoxycarbonyloxy, aminoalkyl, mono-amido and amidoalkyl;

wherein $R^7$ is selected from carboxyl, n-propyl, n-butyl, amido and methylthiomethyl;
wherein $R^8$ is hydrido or methyl;
wherein $R^9$ is selected from hydrido, lower alkyl, methoxy and phenyl;
wherein $R^{10}$ is hydroxy;
wherein $R^{11}$ is hydrido or methyl;
wherein $R^{12}$ is selected from lower alkyl, phenyl, phenylethyl, cyclohexylethyl,

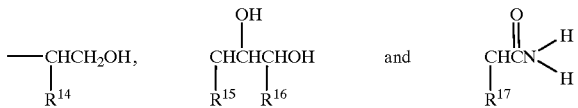

wherein each of $R^{14}$ through $R^{17}$ is independently selected from hydrido, hydroxy, methyl, ethyl, n-propyl, isopropyl, n-butyl, isobutyl, benzyl and phenyl; or a pharmaceutically-acceptable amide, ester or salt thereof.

4. A compound of claim 3 wherein $R^1$ is phenyl or cyclohexyl; wherein $R^2$ is hydrido or methyl; wherein $R^3$ is selected from hydrido, hydroxy, acetyl(Lys)NH—, acetyl (Tyr)NH—, acetyl (Thr)NH—, acetylamino, propionylamino and benzyloxycarbonylamino; wherein $R^4$ is hydrido; wherein $R^5$ is selected from isopropyl, isobutyl, n-propyl, n-butyl, aminopropyl, aminobutyl, phenyl, benzyl, para-hydroxyphenyl, para-hydroxybenzyl, imidazolcarbonylethyl, imidazolcarbonylpropyl, pyrrolidinylcarbonylethyl, pyrrolidinylcarbonylpropyl, azetidinylcarbonylethyl, azetidinylcarbonylpropyl, morpholinocarbonylethyl, morpholinocarbonylpropy, piperazinocarbonylethyl, piperazinocarbonylpropyl, pyridinylcarbonylethyl, pyridinylcarbonylpropyl, oxazolylcarbonylethyl, oxazolylcarbonylpropyl, isoxazolylcarbonylethyl, isoxazolylcarbonylpropyl, azepinylcarbonylethyl and azepinylcarbonylethyl; wherein $R^6$ is selected from hydrido, methyl, hydroxy, methoxy, phenyl and aminocarbonyl; wherein $R^7$ is carboxyl or methylthiomethyl; wherein $R^8$ is hydrido; wherein $R^9$ is selected from hydrido, hydroxy, methyl, methoxy and phenyl; wherein $R^{10}$ is hydroxy; wherein $R^{11}$ is methyl; wherein $R^{12}$ is selected from methyl, ethyl, propyl, butyl, isobutyl, —CH(iBu)CH$_2$OH and —CH(iBu)CONH$_2$; or a pharmaceutically-acceptable amide, ester or salt thereof.

5. A compound of claim 4 which is

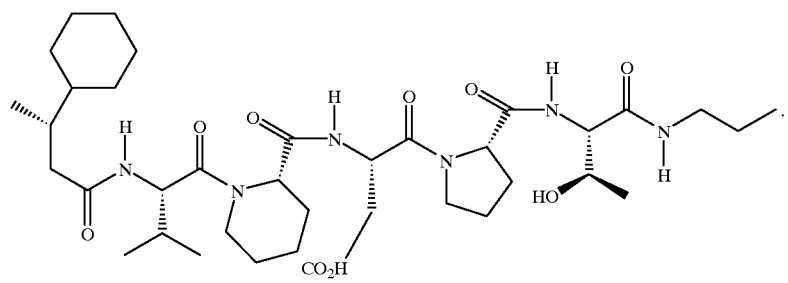

6. A compound of claim 4 which is
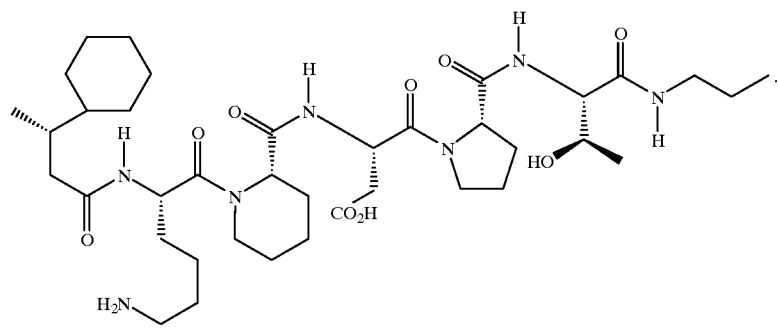
7. A compound of claim 4 which is
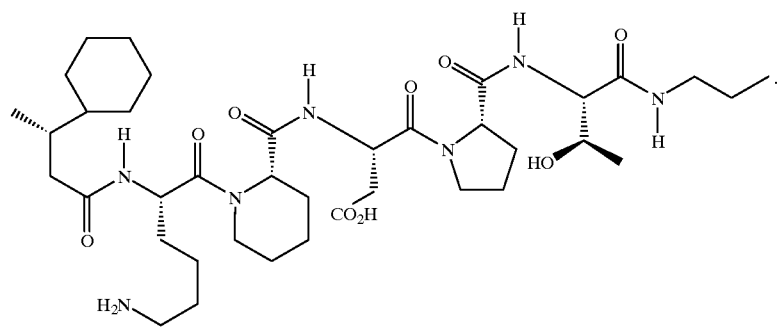
8. A compound of claim 4 which is
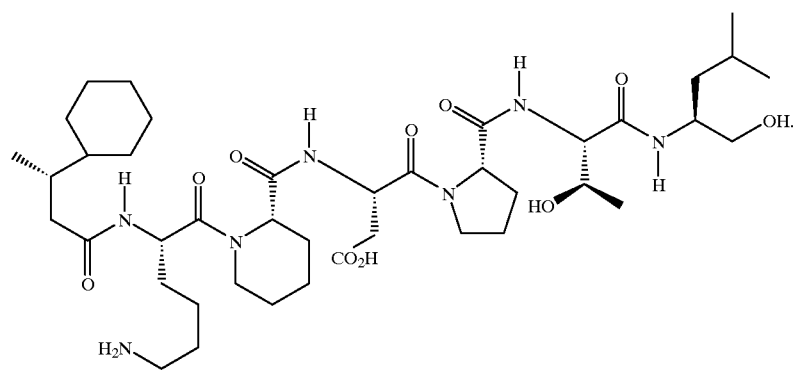
* * * * *